United States Patent
Linke et al.

(10) Patent No.: US 9,580,461 B2
(45) Date of Patent: Feb. 28, 2017

(54) METHOD FOR PURIFYING ACTIVE POLYPEPTIDES OR IMMUNOCONJUGATES

(75) Inventors: Thomas Linke, Odenton, MD (US); William K. Wang, McLean, VA (US); Ambarish Shah, Boyds, MD (US); Hasige Sathish, Germantown, MD (US); Alan Hunter, Gaithersburg, MD (US); Christopher Thompson, Gaithersburg, MD (US)

(73) Assignee: MedImmune, LLC, Gaithersburg, MD (US)

( * ) Notice: Subject to any disclaimer, the term of this patent is extended or adjusted under 35 U.S.C. 154(b) by 252 days.

(21) Appl. No.: 13/813,083

(22) PCT Filed: Jul. 27, 2011

(86) PCT No.: PCT/US2011/045524
§ 371 (c)(1),
(2), (4) Date: Apr. 8, 2013

(87) PCT Pub. No.: WO2012/015912
PCT Pub. Date: Feb. 2, 2012

(65) Prior Publication Data
US 2013/0202626 A1    Aug. 8, 2013

Related U.S. Application Data

(60) Provisional application No. 61/369,148, filed on Jul. 30, 2010.

(51) Int. Cl.
| | |
|---|---|
| *A61K 49/00* | (2006.01) |
| *A61K 39/395* | (2006.01) |
| *A61K 39/00* | (2006.01) |
| *C07K 1/18* | (2006.01) |
| *B01D 15/16* | (2006.01) |
| *B01D 15/36* | (2006.01) |
| *B01J 41/14* | (2006.01) |
| *B01J 41/20* | (2006.01) |
| *C07K 17/02* | (2006.01) |
| *A61K 47/48* | (2006.01) |
| *C07K 16/28* | (2006.01) |

(52) U.S. Cl.
CPC .......... *C07K 1/18* (2013.01); *A61K 47/48484* (2013.01); *A61K 47/48561* (2013.01); *B01D 15/166* (2013.01); *B01D 15/363* (2013.01); *B01J 41/14* (2013.01); *B01J 41/20* (2013.01); *C07K 16/2803* (2013.01); *C07K 17/02* (2013.01); *C07K 2317/94* (2013.01); *C07K 2319/55* (2013.01)

(58) Field of Classification Search
CPC ........ A61K 39/00; A61K 39/02; A61K 47/00; A61K 47/48; C07K 16/00; C07K 16/18; C07K 16/28; C07K 2319/00; C07K 2319/55
USPC ..... 424/9.1, 9.2, 130.1, 143.1, 178.1, 179.1, 424/183.1
See application file for complete search history.

(56) References Cited

U.S. PATENT DOCUMENTS

| | | |
|---|---|---|
| 7,355,012 B2 * | 4/2008 | Pastan et al. ............... 530/387.3 |
| 7,541,034 B1 | 6/2009 | Fitzgerald et al. |
| 2005/0118182 A1 | 6/2005 | Pastan et al. |
| 2007/0189962 A1 | 8/2007 | Pastan et al. |
| 2008/0125363 A1 | 5/2008 | Filpula et al. |
| 2010/0129379 A1 | 5/2010 | Carpenter et al. |

FOREIGN PATENT DOCUMENTS

| | | |
|---|---|---|
| WO | WO 2005/052006 | 6/2005 |
| WO | 2009149281 A1 | 12/2009 |
| WO | 03051926 A1 | 5/2010 |

OTHER PUBLICATIONS

International Search Report mailed Dec. 20, 2011, in International Application No. PCT/US2011/045524, filed Jul. 27, 2011.
Kreitman, Robert J. et al,. "Immunotoxins for targeted cancer therapy," AAPS Journal, American Association of Pahrmaceutical Scientists, 8(3): E532-E551 (2006).
Kreitman, Robert J. et al., "Cytotoxic activity of disulfide-stabilized recombinant immunotoxin RFB4 (dsFv)-PE38 (BL22) twoard fresh malignant cells from patients with B-cell leukemias," Clinical Cancer Research, The American Association for Cancer Research, 6(4): 1476-1487 (2000).

* cited by examiner

*Primary Examiner* — Rodney P Swartz

(57) ABSTRACT

The present invention provides methods for isolating an active polypeptide or immunoconjugate by purification of a solution containing both the active polypeptide or immunoconjugate and an acidic variant thereof, such as a deamidated variant, using anion exchange chromatography.

16 Claims, 6 Drawing Sheets

Figure 1:
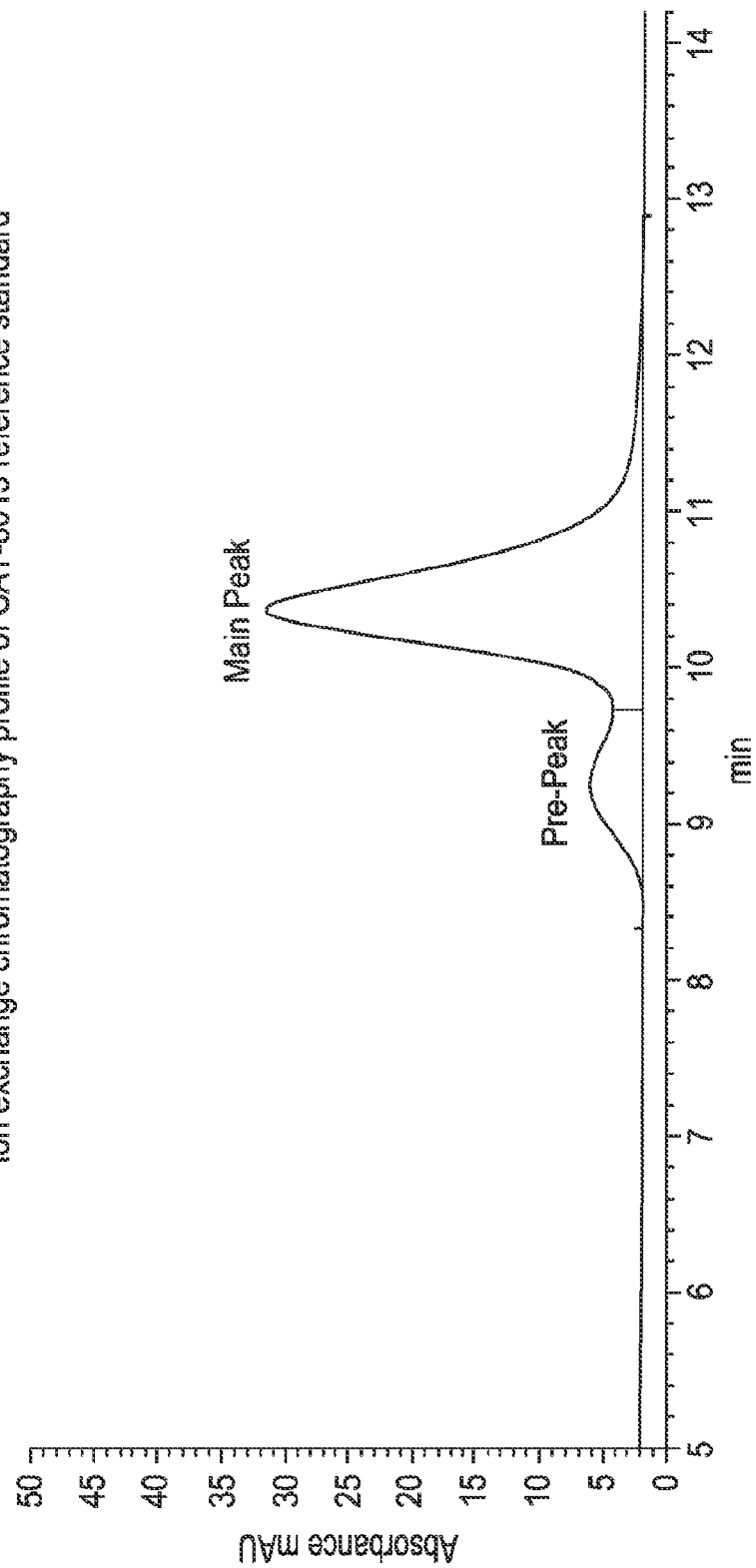

Correlation between % Relative Potency and % Pre-Peak

SDS-PAGE Analysis of QHP
Load and Eluate Pool Samples

Large Scale Purification of CAT-8015 on QHP

SDS-PAGE Analysis of QHP Load and Eluate Pool Samples

Percent Pre-Peak in HA Product as a Function of Solubilization pH

METHOD FOR PURIFYING ACTIVE POLYPEPTIDES OR IMMUNOCONJUGATES

CROSS-REFERENCE TO RELATED APPLICATIONS

This application is a U.S. National Stage application of International Application No. PCT/US2011/045524, filed on Jul. 27, 2011, said International Application No. PCT/US2011/045524 claims benefit under 35 U.S.C. §119(e) of U.S. Provisional Application No. 61/369,148, filed Jul. 30, 2010. Each of the above listed applications is incorporated by reference herein in its entirety for all purposes.

REFERENCE TO THE SEQUENCE LISTING

This application incorporates by reference a Sequence Listing submitted with this application as text file entitled MOXE-300_Seq, created on Jan. 28, 2013, and having a size of 40 kilobytes.

BACKGROUND OF THE INVENTION

Field of the Invention

The present invention provides methods for purifying an active polypeptide or immunoconjugate from a solution containing the polypeptide or immunoconjugate and an acidic variant thereof, wherein said acidic variant is a deamidated species of said polypeptide or immunoconjugate. The present invention also provides formulations containing such purified polypeptides or immunoconjugates.

Background Art

The large-scale, economic purification of proteins is a factor for the biopharmaceutical industry. Therapeutic proteins are typically produced using prokaryotic or eukaryotic cell lines that are engineered to express the protein of interest from a recombinant plasmid containing the gene encoding the protein. Separation of the desired protein from the mixture of components fed to the cells and cellular by-products to an adequate purity, e.g., sufficient for use as a human therapeutic, poses a formidable challenge to biologics manufacturers for several reasons.

Manufacturers of protein-based pharmaceutical products must comply with strict regulatory standards, including extremely stringent purity requirements. To ensure safety, regulatory agencies, such as Food and Drug Administration (FDA), require that protein-based pharmaceutical products are substantially free from impurities, including both product related contaminants such as aggregates, fragments and variants of the recombinant protein and process related contaminants such as host cell proteins, media components, viruses, DNA and endotoxins. While various protein purification schemes are available and widely used in the biopharmaceutical industry, they typically include an affinity-purification step, such as Protein A purification in the case of antibodies, in order to reach a pharmaceutically acceptable degree of purity.

The development of a purification scheme applicable to a particular biomolecule or various biomolecules that is scaleable, controllable, and that strategically employs the use of particular resins or a combination of resins will allow its integration into product development at a very early stage in overall drug development. This approach to the design of a purification scheme can minimize costly changes to manufacturing processes which may otherwise be necessary later in drug development or, worse, after approval. As the process is scaled-up and approaches good manufacturing practices (GMP) production conditions, additional inherent complexities arise, including those associated with resin packing and buffer preparation. The manufacturing process, and its capacity, can be improved by simplifying the purification scheme, by eliminating process steps and maximizing throughput and productivity, while maintaining the integrity and purity of the molecule that is being purified. Therefore, it would be desirable and advantageous to start with a simple and efficient process that can produce a drug substance of high quality and safety.

One complexity associated with the purification of a drug product is the maintenance of potency throughout the purification process. Many factors can contribute to a reduction or inhibition of potency, including the modification of the drug product during the development process. Such modification can occur at various stages of the process, for example, when the protein is being expressed in the cell, or when a protein that has been isolated from a cell is subject to various conditions or buffers. The present invention provides a method for purifying an active polypeptide or immunoconjugate from a solution containing a modified variant of the polypeptide or immunoconjugate, where the presence of this modified variant results in an inhibition in potency of the final drug product.

BRIEF SUMMARY OF THE INVENTION

The present invention provides a method of purifying a polypeptide of interest from a solution containing the polypeptide and an acidic variant, such as a deamidated variant, of the polypeptide.

In particular, the present invention provides a method of purifying an active immunoconjugate, where the immunoconjugate is deamidated at one or more residues, and wherein the deamidation results in an inhibition of potency of said immunoconjugate, the method comprising: (a) contacting the immunoconjugate with an anion exchange AIEX chromatography matrix; and (b) eluting the bound immunoconjugate from the AIEX chromatography matrix with a high salt buffer, thereby separating the active immunoconjugate from the deamidated variant.

The invention also provides a method of producing a purified polypeptide from a solution comprising the polypeptide and an acidic variant of the polypeptide, where the acidic variant of the polypeptide results in an inhibition of potency of the polypeptide, the method comprising: (a) contacting the polypeptide with an anion exchange (AIEX) chromatography matrix; and (b) eluting the bound polypeptide from the AIEX chromatography matrix with a high salt buffer, thereby separating said polypeptide from the acidic variant and producing a purified polypeptide.

The invention further provides a method of producing a purified polypeptide or immunoconjugate from a solution comprising the polypeptide and an acidic variant of the polypeptide, the method comprising: (a) producing the polypeptide or immunoconjugate in a bacterial cell which expresses the polypeptide or immunoconjugate; (b) isolating inclusion bodies containing the polypeptide or immunoconjugate from the bacterial cells; (c) refolding the polypeptide or immunoconjugate isolated from the inclusion bodies; (d) contacting the composition containing the polypeptide or immunoconjugate with an AIEX chromatography matrix; and (b) eluting the bound polypeptide or immunoconjugate from the AIEX chromatography matrix with a high salt buffer, thereby purifying the polypeptide or immunoconjugate from the solution.

In certain embodiments, the acidic variant is a deamidated variant. In further embodiments, between about 75 to about 99% of the acidic or deamidated variant is removed during the purification process, in particular about 75%, 80%, 85%, 90%, 95%, 96%, 97%, 98% or 99%.

The AIEX matrix of the invention contains quaternary amine or tertiary amine ion exchange groups, a quaternary amino (Q) group, In certain embodiments, the AIEX matrix is Q sepharose.

The polypeptide or immunoconjugate of the invention is eluted with a linear or step salt gradient. In certain embodiments, the linear salt gradient is from about 150 mM NaCl in Tris/HCl, pH 8.0 to about 300 mM NaCl in Tris/HCl, pH 8.0, from about 175 mM NaCl in Tris/HCl, pH 8.0 to about 275 mM NaCl in Tris/HCl, pH 8.0, or from about 192 mM NaCl in Tris/HCl, pH 8.0 to about 245 mM NaCl in Tris/HCl, pH 8.0.

In one embodiment, the polypeptide or immunoconjugate of the invention comprises an antibody or antigen binding fragment thereof, where the antibody or antigen binding fragment comprises a Fab, a Fab', a F(ab')2, a Fd, a single chain Fv or scFv, a disulfide linked Fv, a V NAR domain, an IgNar, an intrabody, an IgG CH2, a minibody, a F(ab')3, a tetrabody, a triabody, a diabody, a single-domain antibody, DVD-Ig, Fcab, mAb2, a (scFv)2, or a scFv-Fc. In certain embodiments, the antibody or antigen binding fragment binds a cell surface receptor, such as the cell surface receptor is CD22. In further embodiments, the antibody or antigen binding fragment thereof comprises a VH and VL sequence, where the VH sequence is selected from the group consisting of SEQ ID NOs: 6-11 and the VL sequence is selected from the group consisting of SEQ ID NOs: 2, and 12-15.

In another embodiment, the polypeptide or immunoconjugate comprises a toxin, where the toxin is selected from the group consisting of: *Pseudomonas* exotoxin, ricin, abrin, diphtheria toxin and subunits thereof, as well as botulinum toxins A through F or variants, or derivatives thereof. In certain embodiments, the *Pseudomonas* exotoxin, or variant thereof has an amino acid sequence selected from the group consisting of SEQ ID NOs:16-22. In a particular embodiment, the immunoconjugate is the CAT-8015 immunotoxin comprising the VH-PE38 subunit of SEQ ID NO:1 and the VL subunit of SEQ ID NO:2.

The invention also provides a composition comprising a purified immunoconjugate having less than between about 25% and about 1% deamidated species, wherein said immunoconjugate is purified by any of the methods described above. The composition can have less than about 25%, 20%, 15%, 10%, 5%, 4%, 3%, 2%, or 1% of the deamidated species present. In certain embodiments, the composition is a pharmaceutical composition comprising a purified polypeptide or immunoconjugate and a pharmaceutically acceptable carrier.

The invention also provides a formulation comprising 1 mg/mL CAT-8015 in 25 mM sodium phosphate, 4% sucrose, 8% glycine, 0.02% polysorbate 80 (PS80), pH 7.4. In further embodiments, the formulation is lyophilized.

The invention also provides a method of modifying the bioactivity of a polypeptide solution comprising a polypeptide and a deamidated variant, the method comprising separating the polypeptide from the deamidated variant by linear elution AIEX chromatography; and combining the purified polypeptide and deamidated variant in fixed quantities to obtain the desired bioactivity of the polypeptide solution.

BRIEF DESCRIPTIONS OF THE DRAWINGS

FIG. 1. A graph depicting an ion exchange chromatography (IEC) profile of a CAT-8015 reference standard. The pre-peak of CAT-8015 represents the majority of inactive deamidated, or iso-deamidated CAT-8015, while the main peak contains the majority of the active, intact CAT-8015 immunoconjugate.

Figure 2:
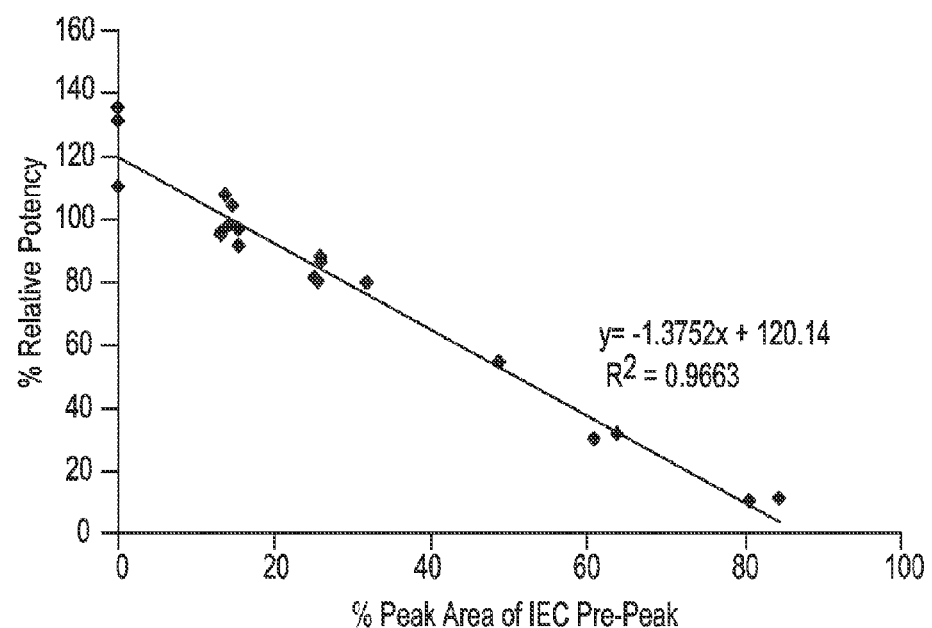

FIG. 2. A graph depicting the correlation between the percent of relative potency of CAT-8015 and the percent of pre-peak in the sample.

Figure 3:
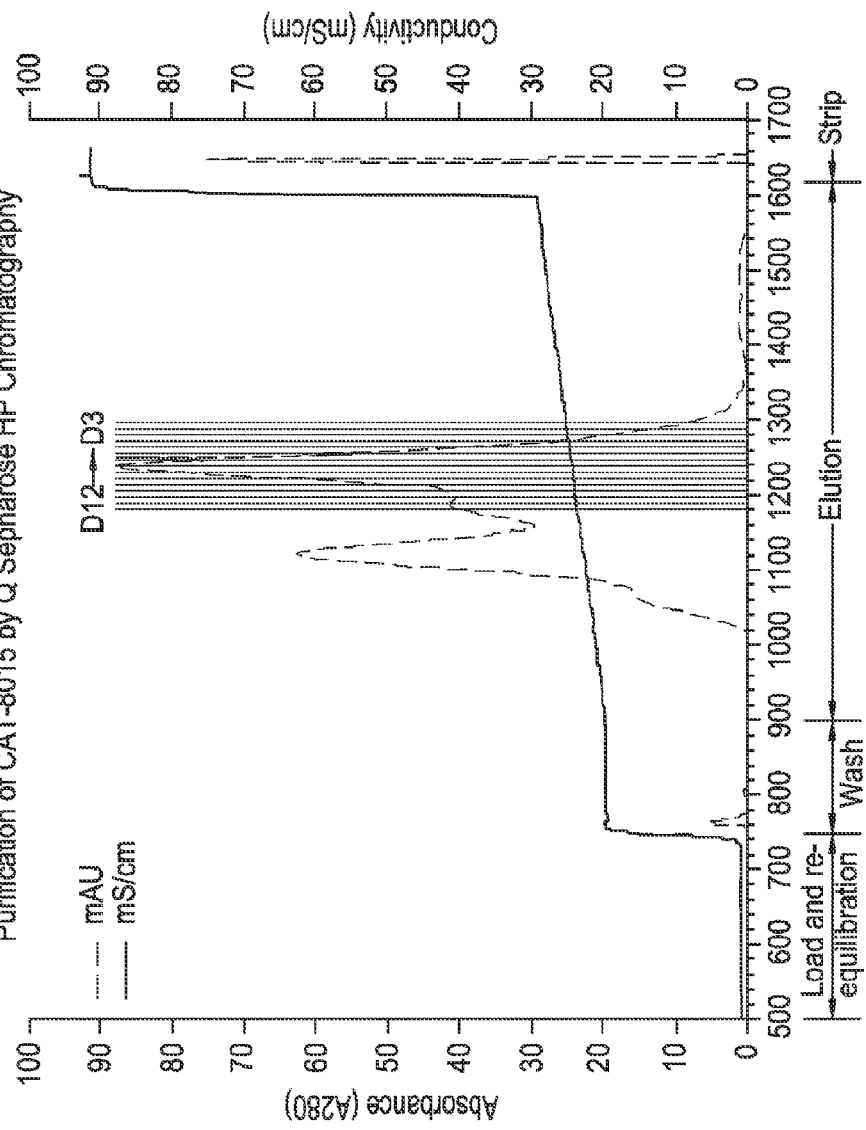

FIG. 3. A graph depicting an elution profile of bench-scale purification of CAT-8015 by Q Sepharose HP Chromatography. CAT-8015 was purified using Q Sepharose HP. The majority of active, intact CAT-8015 resided in fractions D5, D7, and D9 (the main peak spanning from D3 to D12 as indicated above the peak).

Figure 4:
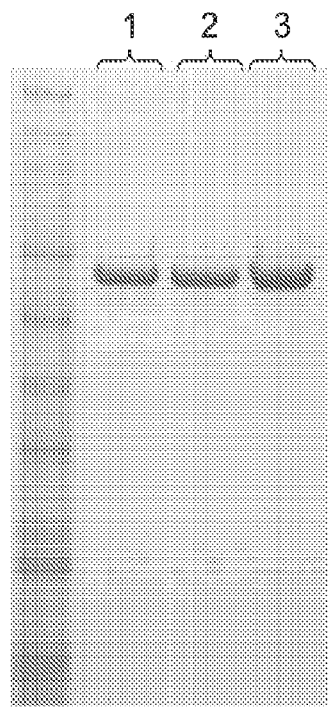

FIG. 4. An SDS-PAGE analysis of QHP load and eluate pool samples (bench-scale purification). Lane 1 corresponds to the QHP load pool; Lane 2 corresponds to the QHP eluate pool; and Lane 3 corresponds to a CAT-8015 reference standard.

Figure 5:
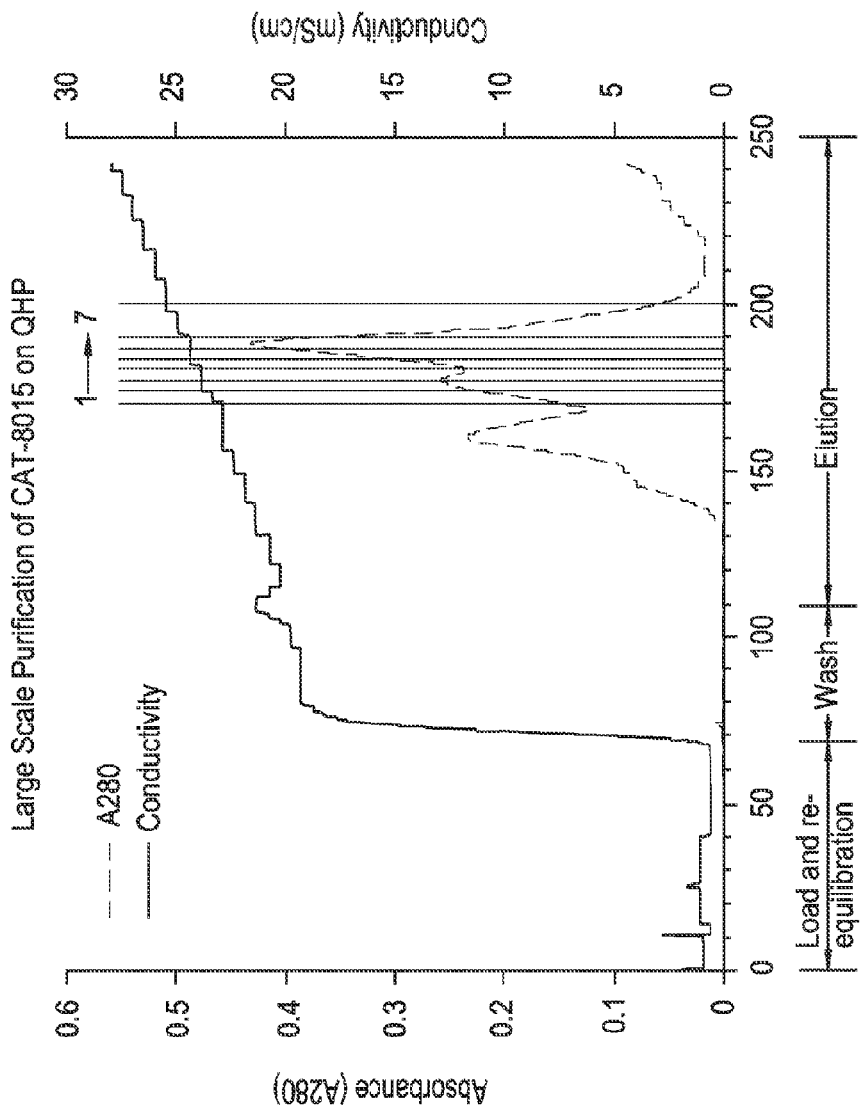

FIG. 5. Large-scale purification of CAT-8015 by Q Sepharose HP Chromatography. CAT-8015 was purified using Q Sepharose HP. As shown in the figure and Table 3, the majority of active, intact CAT-8015 resided in fractions 5, 6, and 7.

Figure 6:
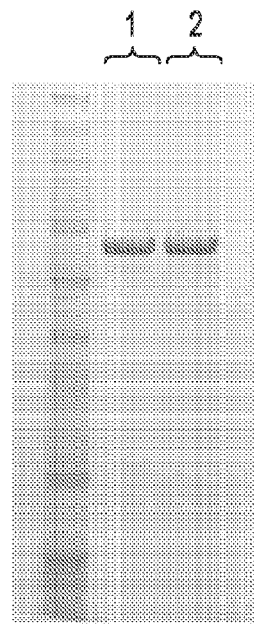

FIG. 6. An SDS-PAGE analysis of QHP load and eluate pool samples (large-scale purification). Lane 1 corresponds to the QHP load pool; and Lane 2 corresponds to the QHP eluate pool.

Figure 7:
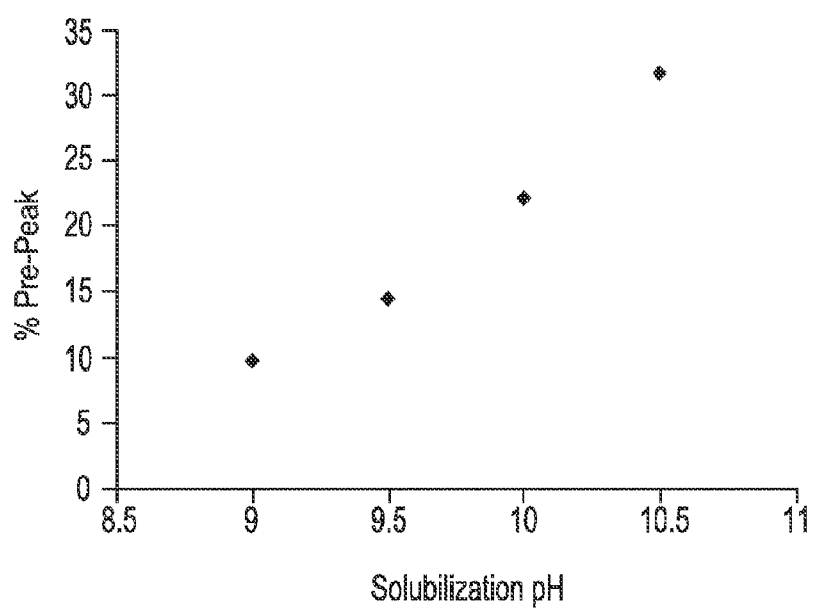

FIG. 7. A graph depicting percent Pre-Peak in HA Product as a Function of Solubilization pH as described in Example 6.

DETAILED DESCRIPTION OF THE INVENTION

The invention provides methods for purifying an active polypeptide or immunoconjugate from a solution containing the polypeptide or immunoconjugate and an acidic variant thereof. In one embodiment, the acidic variant comprises a deamidated form of the polypeptide or immunoconjugate. In contrast to the expected elution behavior from an anion exchange column, the bulk of deamidated variants elute prior to intact polypeptides under salt gradient elution conditions. Details of the methods are provided herein.

The terms "polypeptide," "peptide," "protein," and "protein fragment" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers.

The term "amino acid" refers to naturally occurring and synthetic amino acids, as well as amino acid analogs and amino acid mimetics that function similarly to the naturally occurring amino acids. Naturally occurring amino acids are those encoded by the genetic code, as well as those amino acids that are later modified, e.g., hydroxyproline, gamma-carboxyglutamate, and O-phosphoserine. Amino acid analogs refers to compounds that have the same basic chemical structure as a naturally occurring amino acid, e.g., an alpha carbon that is bound to a hydrogen, a carboxyl group, an amino group, and an R group, e.g., homoserine, norleucine, methionine sulfoxide, methionine methyl sulfonium. Such analogs can have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions similarly to a naturally occurring amino acid. Negatively charged amino acids include aspartic acid (or aspartate) and glutamic acid (or glutamate). Positively charged amino acids include arginine, histidine, and lysine.

The "composition" to be purified herein comprises the polypeptide of interest and one or more impurities. The composition may be "partially purified" (i.e., having been subjected to one or more purification steps, such as by non-affinity chromatography described herein or may be obtained directly from a host cell or organism producing the polypeptide (e.g., the composition may comprise harvested cell culture fluid).

The terms "polypeptide" or "polypeptide of interest" or "protein of interest" and "target protein" or "protein" are used interchangeably and refer to a protein or polypeptide such as an antibody or immunoconjugate (as defined herein) that is to be purified by a method of the invention from a mixture of proteins and, other materials such as an acidic variant of the polypeptide of interest.

An "acidic variant" is a variant of a polypeptide or immunoconjugate which is more acidic (e.g., as determined by cation exchange chromatography) than the polypeptide of interest. An example of an acidic variant is a deamidated variant.

Deamidated proteins are those that have had some or all of the free amide functional groups hydrolyzed to carboxylic acids, such as conversion of glutamines to glutamic acid. The rate of this reaction is dependent on the primary sequence, three-dimensional structure, pH, temperature, buffer type, ionic strength and other solution properties Importantly, the deamidation reaction introduces a negative charge into the molecule. As described further below, the protein deamidation can have a negative impact on protein activity.

As used herein, the terms "antibody" and "immunoglobulin" are used interchangeably in the broadest sense and include monoclonal antibodies (e.g., full length or intact monoclonal antibodies), polyclonal antibodies, multivalent antibodies, multispecific antibodies (e.g., bispecific antibodies so long as they exhibit the desired biological activity) and antibody fragments as described herein. The term "bispecific antibody" is intended to include any antibody that has two different binding specificities, i.e., the antibody binds two different epitopes, which can be located on the same target antigen or, more commonly, on different target antigens.

Native antibodies and immunoglobulins are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end. The constant domain of the light chain is aligned with the first constant domain of the heavy chain, and the light chain variable domain is aligned with the variable domain of the heavy chain. Particular amino acid residues are believed to form an interface between the light and heavy chain variable domains (Clothia et al., *J. Mol. Biol.* 186, 651-66, (1985); Novotny and Haber, *Proc. Natl. Acad. Sci. USA* 82, 4592-4596 (1985)). Five human immunoglobulin classes are defined on the basis of their heavy chain composition, and are named IgG, IgM, IgA, IgE, and IgD. The IgG-class and IgA-class antibodies are further divided into subclasses, namely, IgG1, IgG2, IgG3, and IgG4, and IgA1 and IgA2. The heavy chains in IgG, IgA, and IgD antibodies have three constant region domains, that are designated CH1, CH2, and CH3, and the heavy chains in IgM and IgE antibodies have four constant region domains, CH1, CH2, CH3, and CH4. Thus, heavy chains have one variable region and three or four constant regions Immunoglobulin structure and function are reviewed, for example, in Harlow et al., Eds., Antibodies: A Laboratory Manual, Chapter 14, Cold Spring Harbor Laboratory, Cold Spring Harbor (1988).

The term "antibody fragment" refers to a portion of an intact antibody and refers to the antigenic determining variable regions of an intact antibody. Examples of antibody fragments include, but are not limited to Fab, Fab', F(ab')2, Fv and single chain Fv fragments, linear antibodies, single chain antibodies, and multispecific antibodies formed from antibody fragments.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific and bind a single antigen. Furthermore, in contrast to polyclonal antibody preparations that typically include different antibodies directed against different determinants (epitopes), each monoclonal antibody is directed against a single determinant on the antigen. That an antibody "selectively binds" or "specifically binds" means that the antibody reacts or associates more frequently, more rapidly, with greater duration, with greater affinity, or with some combination of the above to an epitope than with alternative substances, including unrelated proteins. "Selectively binds" or "specifically binds" means, for instance, that an antibody binds to a protein with a $K_D$ of at least about 0.1 mM, but more usually at least about 1 μM. "Selectively binds" or "specifically binds" means at times that an antibody binds to a protein at times with a $K_D$ of at least about 0.1 μM or better, and at other times at least about 0.01 μM or better. Because of the sequence identity between homologous proteins in different species, specific binding can include an antibody that recognizes a tumor cell marker protein in more than one species.

The antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816, 567; and Morrison et al, *Proc. Natl. Acad. Sci. USA* 81:6851-6855 (1984)).

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies can comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally will also comprise at least a portion of an immunoglobulin constant region (Fc), typically that of a human immunoglobulin. For further details, see Jones et al., *Nature* 321:522-525 (1986); Riechmann et al., *Nature* 332:323-329 (1988); and Presta, *Curr. Op. Struct. Biol.* 2:593-596 (1992). See also the following review articles and references cited therein: Vaswani and Hamilton, *Ann. Allergy, Asthma & Immunol.* 1:105-115 (1998); Harris, *Biochem. Soc. Transactions* 23: 1035-1038 (1995); Hurle and Gross, *Curr. Op. Biotech.* 5:428-433 (1994).

A "human antibody" is one that possesses an amino acid sequence that corresponds to that of an antibody produced by a human and/or has been made using any of the techniques for making human antibodies as disclosed herein. This definition of a human antibody specifically excludes a humanized antibody comprising non-human antigen-binding residues.

The term "immunoconjugate" or "conjugate" or "immunotoxin" as used herein refers to a compound or a derivative thereof that is linked to a cell binding agent (e.g., an anti-CD22 antibody or fragment thereof) and is defined by a generic formula: C-L-A, wherein C=cytotoxin, L=linker, and A=cell binding agent (e.g., anti-CD22 antibody or antibody fragment) Immunoconjugates can also be defined by the generic formula in reverse order: A-L-C.

The term "cytotoxin" or "cytotoxic agent" as used herein refers to a substance that inhibits or prevents the function of cells and/or causes destruction of cells. The term is intended to include radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents e.g., methotrexate, adriamicin, vinca alkaloids (vincristine, vinblastine, etoposide), doxorubicin, melphalan, mitomycin C, chlorambucil, daunorubicin or other intercalating agents, enzymes and fragments thereof such as nucleolytic enzymes, antibiotics, and toxins such as small molecule toxins or enzymatically active toxins of bacterial, fungal, plant or animal origin, including fragments and/or variants thereof, and the various antitumor or anticancer agents disclosed below. Examples of cytotoxic agents include, but are not limited to, abrin, ricin, *Pseudomonas* exotoxin (PE), diphtheria toxin (DT), botulinum toxin, or modified toxins thereof. For example, PE and DT are highly toxic compounds that typically bring about death through liver toxicity. PE and DT, however, can be modified into a form for use as an immunotoxin by removing the native targeting component of the toxin (e.g., domain 1a of PE or the B chain of DT) and replacing it with a different targeting moiety, such as an antibody.

In some embodiments, the toxin is *Pseudomonas* exotoxin. *Pseudomonas* exotoxin A (PE) is an extremely active monomeric protein (molecular weight 66 kD), secreted by *Pseudomonas aeruginosa*, which inhibits protein synthesis in eukaryotic cells through the inactivation of elongation factor 2 (EF-2) by catalyzing its ADP-ribosylation (catalyzing the transfer of the ADP ribosyl moiety of oxidized NAD onto EF-2).

The toxin contains three structural domains that act in concert to cause cytotoxicity. Domain Ia (amino acids 1-252) mediates cell binding. Domain II (amino acids 253-364) is responsible for translocation into the cytosol and domain III (amino acids 400-613) mediates ADP ribosylation of elongation factor 2, which inactivates the protein and causes cell death. The function of domain Ib (amino acids 365-399) remains undefined, although a large part of it, amino acids 365-380, can be deleted without loss of cytotoxicity. See Siegall et al., *J. Biol. Chem.* 264: 14256-14261 (1989).

The *Pseudomonas* exotoxins (PE) employed in the present invention include the native sequence, cytotoxic fragments of the native sequence, and conservatively modified variants of native PE and its cytotoxic fragments. Cytotoxic fragments of PE include those which are cytotoxic with or without subsequent proteolytic or other processing in the target cell (e.g., as a protein or pre-protein). Cytotoxic fragments of PE include PE40, PE38, and PE35. PE40 is a truncated derivative of PE as previously described in the art. See, Pai et al., *Proc. Natl. Acad. Sci. USA*, 88:3358-62 (1991); Kondo et al., *J. Biol. Chem.* 263:9470-9475 (1988). PE38 is a truncated PE composed of amino acids 253-364 and 381-613 of native PE. PE35 is a 35 kD carboxyl-terminal fragment of PE composed of a Met at position 280 followed by amino acids 281-364 and 381-613 of native PE. In one embodiment, the cytotoxic fragment PE38 is employed. PE38 is a pro-protein which can be activated to its cytotoxic form upon processing within a cell.

A "PE immunoconjugate" or "PE immunotoxin" is an immunoconjugate or immunotoxin comprising an antibody or antigen binding fragment thereof and a PE toxin or variant thereof.

By "purifying" a polypeptide or immunoconjugate from a composition comprising the polypeptide and one or more impurities is meant increasing the degree of purity of the polypeptide in the composition by removing (completely or partially) at least one impurity from the composition. According to the present invention, purification is performed without the use of an affinity chromatography step.

The term "chromatography" refers to the process by which a solute of interest in a mixture is separated from other solutes in a mixture as a result of differences in rates at which the individual solutes of the mixture migrate through a stationary medium under the influence of a moving phase, or in bind and elute processes.

The term "ion-exchange" and "ion-exchange chromatography" refers to the chromatographic process in which a solute of interest (such as a protein) in a mixture interacts with a charged compound linked (such as by covalent attachment) to a solid phase ion exchange material such that the solute of interest interacts non-specifically with the charged compound more or less than solute impurities or contaminants in the mixture. The contaminating solutes in the mixture elute from a column of the ion exchange material faster or slower than the solute of interest or are bound to or excluded from the resin relative to the solute of interest. "Ion-exchange chromatography" specifically includes cation exchange, anion exchange, and mixed mode chromatography.

The phrase "ion exchange material" refers to a solid phase that is negatively charged (i.e., a cation exchange resin) or positively charged (i.e., an anion exchange resin). The charge may be provided by attaching one or more charged ligands to the solid phase, e.g., by covalent linking. Alternatively, or in addition, the charge may be an inherent property of the solid phase (e.g., as is the case for silica, which has an overall negative charge).

An "anion exchange resin" refers to a solid phase which is positively charged, thus having one or more positively charged ligands attached thereto. Any positively charged ligand attached to the solid phase suitable to form the anionic exchange resin can be used, such as quaternary amino groups Commercially available anion exchange resins include DEAE cellulose, Poros PI 20, PI 50, HQ 10, HQ 20, HQ 50, D 50 from Applied Biosystems, Sartobind Q from Sartorius, MonoQ, MiniQ, Source 15Q and 30Q, Q, DEAE and ANX Sepharose Fast Flow, Q Sepharose High Performance, QAE SEPHADEX™ and FAST Q SEPHAROSE™ (GE Healthcare), WP PEI, WP DEAM, WP QUAT from J. T. Baker, Hydrocell DEAE and Hydrocell QA from Biochrom Labs Inc., UNOsphere Q, Macro-Prep DEAE and Macro-Prep High Q from Biorad, Ceramic HyperD Q, ceramic HyperD DEAE, Trisacryl M and LS DEAE, Spherodex LS DEAE, QMA Spherosil LS, QMA Spherosil M and Mustang Q from Pall Technologies, DOWEX Fine Mesh Strong Base Type I and Type II Anion Resins and DOWEX MONOSPHER E 77, weak base anion from Dow Liquid Separations, Intercept Q membrane, Matrex Cellufine A200, A500, Q500, and Q800, from Millipore, Fractogel EMD TMAE, Fractogel EMD DEAE and Fractogel EMD DMAE from EMD, Amberlite weak strong anion exchangers type I and II, DOWEX weak and strong anion exchangers type I and II, Diaion weak and strong anion exchangers type I and II, Duolite from Sigma-Aldrich, TSK gel Q and DEAE 5PW and 5PW-HR, Toyopearl SuperQ-650S, 650M and 650C, QAE-550C and 650S, DEAE-650M and 650C from Tosoh, QA52, DE23, DE32, DE51, DE52, DE53, Express-Ion D and Express-Ion Q from Whatman.

By "solid phase" is meant a non-aqueous matrix to which one or more charged ligands can adhere. The solid phase may be a purification column, a discontinuous phase of discrete particles, a membrane, or filter etc. Examples of materials for forming the solid phase include polysaccharides (such as agarose and cellulose); and other mechanically stable matrices such as silica (e.g., controlled pore glass), poly(styrenedivinyl)benzene, polyacrylamide, ceramic particles and derivatives of any of the above.

The term "specific binding" as used herein, such as to describe interactions between a molecule of interest and a ligand bound to a solid phase matrix, refers to the generally reversible binding of a protein of interest to a ligand through the combined effects of spatial complementarity of protein and ligand structures at a binding site coupled with electrostatic forces, hydrogen bonding, hydrophobic forces, and/or van der Waals forces at the binding site. The greater the spatial complementarity and the stronger the other forces at the binding site, the greater will be the binding specificity of a protein for its respective ligand. Non-limiting examples of specific binding includes antibody-antigen binding, enzyme-substrate binding, enzyme-cofactor binding, metal ion chelation, DNA binding protein-DNA binding, regulatory protein-protein interactions, and the like.

The term "non-specific binding" as used herein, such as to describe interactions between a molecule of interest and a ligand or other compound bound to a solid phase matrix, refers to binding of a protein of interest to the ligand or compound on a solid phase matrix through electrostatic forces, hydrogen bonding, hydrophobic forces, and/or van der Waals forces at an interaction site, but lacking structural complementarity that enhances the effects of the non-structural forces. Examples of non-specific interactions include, but are not limited to, electrostatic, hydrophobic, and van der Waals forces as well as hydrogen bonding.

A "salt" is a compound formed by the interaction of an acid and a base. A salt useful for the invention include, but are not limited to acetate (e.g., sodium acetate), citrate (e.g., sodium citrate), chloride (e.g., sodium chloride), sulphate (e.g., sodium sulphate), or a potassium salt.

The term "detergent" refers to ionic and nonionic surfactants such as polysorbates (e.g., polysorbates 20 or 80); poloxamers (e.g., poloxamer 188); Triton; sodium dodecyl sulfate (SDS); sodium laurel sulfate; sodium octyl glycoside; lauryl-, myristyl-, linoleyl-, or stearyl-sulfobetaine; lauryl-, myristyl-, linoleyl- or stearyl-sarcosine; linoleyl-, myristyl-, or cetyl-betaine; lauroamidopropyl-, cocamidopropyl-, linoleamidopropyl-, myristamidopropyl-, palmidopropyl-, or isostearamidopropyl-betaine (e.g., lauroamidopropyl); myristamidopropyl-, palmidopropyl-, or isostearamidopropyl-dimethylamine; sodium methyl cocoyl-, or disodium methyl oleyl-taurate; and the MONAQUAT™ series (Mona Industries, Inc., Paterson, N.J.). A useful detergent is a polysorbate, such as polysorbate 20 (TWEEN 20®) or polysorbate 80 (TWEEN 80®).

A "buffer" used in the present invention is a solution that resists changes in pH by the addition of acid or base by the action of its acid-base conjugates components. Various buffers can be employed in a method of the present invention depending on the desired pH of the buffer and the particular step in the purification process [see Buffers. A Guide for the Preparation and Use of Buffers in Biological Systems, Gueffroy, D., ed. Calbiochem Corporation (1975)]. Non-limiting examples of buffer components that can be used to control the pH range desirable for a method of the invention include acetate, citrate, histidine, phosphate, ammonium buffers such as ammonium acetate, succinate, MES, CHAPS, MOPS, MOPSO, HEPES, Tris, and the like, as well as combinations of these TRIS-malic acid-NaOH, maleate, chloroacetate, formate, benzoate, propionate, pyridine, piperazine, ADA, PIPES, ACES, BES, TES, tricine, bicine, TAPS, ethanolamine, CHES, CAPS, methylamine, piperidine, O-boric acid, carbonic acid, lactic acid, butaneandioic acid, diethylmalonic acid, glycylglycine, HEPPS, HEPPSO, imidazole, phenol, POPSO, succinate, TAPS, amine-based, benzylamine, trimethyl or dimethyl or ethyl or phenyl amine, ethylenediamine, or morpholine Additional components (additives) can be present in a buffer as needed, e.g., salts can be used to adjust buffer ionic strength, such as sodium chloride, sodium sulfate and potassium chloride; and other additives such as amino acids (such as glycine and histidine), chaotropes (such as urea), alcohols (such as ethanol, mannitol, glycerol, and benzyl alcohol), detergents (see supra.), and sugars (such as sucrose, mannitol, maltose, trehalose, glucose, and fructose). The buffer components and additives, and the concentrations used, can vary according to the type of chromatography practiced in the invention.

The "loading buffer" is that which is used to load the composition comprising the polypeptide molecule of interest and one or more impurities onto the ion exchange resin. The loading buffer has a conductivity and/or pH such that the polypeptide molecule of interest (and generally one or more impurities) is/are bound to the ion exchange resin or such that the protein of interest flows through the column while the impurities bind to the resin.

The term "wash buffer" when used herein refers to a buffer used to wash or re-equilibrate the ion exchange resin, prior to eluting the polypeptide molecule of interest. Conveniently, the wash buffer and loading buffer may be the same, but this is not required.

The "elution buffer" is used to elute the polypeptide of interest from the solid phase. The conductivity and/or pH of the elution buffer is/are such that the polypeptide of interest is eluted from the ion exchange resin.

The "pI" or "isoelectric point" of a polypeptide refer to the pH at which the polypeptide's positive charge balances its negative charge. pI can be calculated from the net charge of the amino acid residues or sialic acid residues of attached carbohydrates of the polypeptide or can be determined by isoelectric focusing.

By "binding" a molecule to an ion exchange material is meant exposing the molecule to the ion exchange material under appropriate conditions (pH/conductivity) such that the molecule is reversibly immobilized in or on the ion exchange material by virtue of ionic interactions between the molecule and a charged group or charged groups of the ion exchange material.

By "washing" the ion exchange material is meant passing an appropriate buffer through or over the ion exchange material.

To "elute" a molecule (e.g., polypeptide or impurity) from an ion exchange material is meant to remove the molecule therefrom by altering the ionic strength of the buffer surrounding the ion exchange material such that the buffer competes with the molecule for the charged sites on the ion exchange material.

As used in the present disclosure and claims, the singular forms "a," "an," and "the" include plural forms unless the context clearly dictates otherwise.

It is understood that wherever embodiments are described herein with the language "comprising," otherwise analogous embodiments described in terms of "consisting of" and/or "consisting essentially of" are also provided.

The term "and/or" as used in a phrase such as "A and/or B" herein is intended to include both "A and B," "A or B," "A," and "B." Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

Pseudomonas Exotoxin and Other Toxins

Toxins can be employed with antibodies of the present invention to yield immunotoxins. Exemplary toxins include ricin, abrin, diphtheria toxin and subunits thereof, as well as botulinum toxins A through F. These toxins are readily available from commercial sources (e.g., Sigma Chemical Company, St. Louis, Mo.). Diphtheria toxin is isolated from *Corynebacterium diphtheriae*. Ricin is the lectin RCA60 from *Ricinus communis* (Castor bean). The term also references toxic variants thereof. For example, see, U.S. Pat. Nos. 5,079,163 and 4,689,401. *Ricinus communis* agglutinin (RCA) occurs in two forms designated $RCA_{60}$ and $RCA_{120}$ according to their molecular weights of approximately 65 and 120 kD, respectively (Nicholson & Blaustein, *J. Biochem. Biophys. Acta* 266:543 (1972)). The A chain is responsible for inactivating protein synthesis and killing cells. The B chain binds ricin to cell-surface galactose residues and facilitates transport of the A chain into the cytosol (Olsnes, et al., *Nature* 249:627-631 (1974) and U.S. Pat. No. 3,060,165).

Abrin includes toxic lectins from *Abrus precalorius*. The toxic principles, abrin a, b, c, and d, have a molecular weight of from about 63 and 67 kD and are composed of two disulfide-linked polypeptide chains A and B. The A chain inhibits protein synthesis; the B-chain (abrin-b) binds to D-galactose residues (see, Funatsu, et al., *Agr. Biol. Chem.* 52:1095 (1988); and Olsnes, *Methods Enzymol.* 50:330-335 (1978)).

In preferred embodiments of the present invention, the toxin is *Pseudomonas* exotoxin (PE). The *Pseudomonas* exotoxin (or exotoxin A) is an exotoxin produced by *Pseudomonas aeruginosa*. The term "*Pseudomonas* exotoxin" as used herein refers to a full-length native (naturally occurring) PE or a PE that has been modified. Such modifications may include, but are not limited to, elimination of domain Ia, various amino acid deletions in domains 1b, II and III, single amino acid substitutions and the addition of one or more sequences at the carboxyl terminus such as KDEL (SEQ ID NO:3) and REDL (SEQ ID NO:4). See Siegall, et al., *J. Biol. Chem.* 264:14256-14261 (1989). In a preferred embodiment, the cytotoxic fragment of PE retains at least 50%, preferably 75%, more preferably at least 90%, and most preferably 95% of the cytotoxicity of native PE. In a most preferred embodiment, the cytotoxic fragment is more toxic than native PE.

Native *Pseudomonas* exotoxin A (PE) is an extremely active monomeric protein (molecular weight 66 kD), secreted by *Pseudomonas aeruginosa*, which inhibits protein synthesis in eukaryotic cells. The native PE sequence is provided in commonly assigned U.S. Pat. No. 5,602,095, incorporated herein by reference. The method of action is inactivation of the ADP-ribosylation of elongation factor 2 (EF-2). The exotoxin contains three structural domains that act in concert to cause cytotoxicity. Domain Ia (amino acids 1-252) mediates cell binding. Domain II (amino acids 253-364) is responsible for translocation into the cytosol and domain III (amino acids 400-613) mediates ADP ribosylation of elongation factor 2. The function of domain 1b (amino acids 365-399) remains undefined, although a large part of it, amino acids 365-380, can be deleted without loss of cytotoxicity. See Siegall, et al., (1989), supra.

PE employed in the present invention include the native sequence, cytotoxic fragments of the native sequence, and conservatively modified variants of native PE and its cytotoxic fragments. PE variants useful in the invention are described in U.S. Pat. No. 7,355,012, and WO 2007/016150 and WO 2009/032954. Cytotoxic fragments of PE include those which are cytotoxic with or without subsequent proteolytic or other processing in the target cell (e.g., as a protein or pre-protein). Cytotoxic fragments of PE include PE40, PE38, and PE35.

In preferred embodiments, the PE has been modified to reduce or eliminate non-specific cell binding, frequently by deleting domain Ia as taught in U.S. Pat. No. 4,892,827, although this can also be achieved, for example, by mutating certain residues of domain Ia. U.S. Pat. No. 5,512,658, for instance, discloses that a mutated PE in which Domain Ia is present but in which the basic residues of domain Ia at positions 57, 246, 247, and 249 are replaced with acidic residues (glutamic acid, or "E")) exhibits greatly diminished non-specific cytotoxicity. This mutant form of PE is sometimes referred to as PE4E.

PE40 is a truncated derivative of PE as previously described in the art, with a deletion of domain Ia of the native PE molecule. See, Pai, et al., *Proc. Nat'l Acad. Sci. USA* 88:3358-62 (1991); and Kondo, et al., *J. Biol. Chem.* 263:9470-9475 (1988). PE35 is a 35 kD carboxyl-terminal fragment of PE in which amino acid residues 1-279 have been deleted and the molecule commences with a met at position 280 followed by amino acids 281-364 and 381-613 of native PE. PE35 and PE40 are disclosed, for example, in U.S. Pat. Nos. 5,602,095 and 4,892,827. PE4E is a form of PE where all of the domains of native PE are present, but where the basic residues of domain Ia at positions 57, 246, 247 and 249 are replaced with acidic residues (glutamine acid, or "E").

In some preferred embodiments, the cytotoxic fragment PE38 is employed. PE38 is a truncated PE pro-protein composed of amino acids 253-364 and 381-613 which is activated to its cytotoxic form upon processing within a cell (see e.g., U.S. Pat. Nos. 5,608,039, 7,355,012, and Pastan et al., Biochim. Biophys. Acta 1333:C$_1$-C$_6$ (1997)).

As noted above, some or all of domain 1b may be deleted, and the remaining portions joined by a linker or directly by a peptide bond. Some of the amino portion of domain II may be deleted. And, the C-terminal end may contain the native sequence of residues 609-613 (REDLK) (SEQ ID NO:5), or may contain a variation found to maintain the ability of the construct to translocate into the cytosol, such as REDL (SEQ ID NO:4) or KDEL (SEQ ID NO:3), and repeats of these sequences. See, e.g., U.S. Pat. Nos. 5,854,044; 5,821,238; and 5,602,095 and WO 99/51643. While in preferred embodiments, the PE is PE4E, PE40, or PE38, any form of PE in which non-specific cytotoxicity has been eliminated or reduced to levels in which significant toxicity to non-targeted cells does not occur can be used in the immunotoxins of the present invention so long as it remains capable of translocation and EF-2 ribosylation in a targeted cell.

Conservatively Modified Variants of PE

Conservatively modified variants of PE or cytotoxic fragments thereof have at least 80% sequence similarity, preferably at least 85% sequence similarity, more preferably at least 90% sequence similarity, and most preferably at least 95% sequence similarity at the amino acid level, with the PE of interest, such as PE38.

The term "conservatively modified variants" applies to both amino acid and nucleic acid sequences. With respect to particular nucleic acid sequences, conservatively modified variants refer to those nucleic acid sequences which encode identical or essentially identical amino acid sequences, or if the nucleic acid does not encode an amino acid sequence, to essentially identical nucleic acid sequences. Because of the degeneracy of the genetic code, a large number of functionally identical nucleic acids encode any given polypeptide. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid.

Pseudomonas exotoxins employed in the invention can be assayed for the desired level of cytotoxicity by assays well known to those of skill in the art. Thus, cytotoxic fragments of PE and conservatively modified variants of such fragments can be readily assayed for cytotoxicity. A large number of candidate PE molecules can be assayed simultaneously for cytotoxicity by methods well known in the art. For example, subgroups of the candidate molecules can be assayed for cytotoxicity. Positively reacting subgroups of the candidate molecules can be continually subdivided and reassayed until the desired cytotoxic fragment(s) is identified. Such methods allow rapid screening of large numbers of cytotoxic fragments or conservative variants of PE.

Anti-CD22/PE Immunoconjugates

In one embodiment, the polypeptide of interest comprises an antibody that specifically binds CD22. "CD22" refers to a lineage-restricted B cell antigen belonging to the Ig superfamily. It is expressed in 60-70% of B cell lymphomas and leukemias and is not present on the cell surface in early stages of B cell development or on stem cells. See, e.g., Vaickus et al., Crit. Rev. Oncol/Hematol. 11:267-297 (1991). In another embodiment, the polypeptide of interest is an antibody fragment that binds CD22 (e.g., Fab, or scFv).

As used herein, the term "anti-CD22" in reference to an antibody, refers to an antibody that specifically binds CD22 and includes reference to an antibody which is generated against CD22. In some embodiments, the CD22 is a primate CD22 such as human CD22. In one embodiment, the antibody is generated against human CD22 synthesized by a non-primate mammal after introduction into the animal of cDNA which encodes human CD22. In a further embodiment, the polypeptide of interest is a CD22 antibody immunoconjugate that comprises the PE38 exotoxin.

One example of a CD22/PE38 immunoconjugate is CAT-8015 described in International Patent Application Publication Nos. WO 98/41641 and WO2003/27135, U.S. Pat. Nos. 7,541,034, 7,355,012, and U.S. Publication No. 2007/0189962, all of which are herein incorporated by reference. CAT-8015 is a recombinant immunotoxin protein composed of an antibody Fv fragment based on the murine anti-CD22 antibody RFB4 fused to a truncated form of the Pseudomonas exotoxin protein, PE38. The anti-CD22 Fv fragment consists of two domains, a V$_L$ and a V$_H$, where the latter was modified to improve binding to the human CD22 target. The CAT-8015 protein is comprised of two independent polypeptides, the V$_L$ chain (SEQ ID NO:2), and the V$_H$ chain, fused at the C-terminus to the PE38 domain (V$_H$-PE38) (SEQ ID NO:1). Other V$_L$ and V$_H$-PE38 sequences useful in this invention are described in U.S. Pat. Nos. 7,541,034, 7,355,012, and 2007/0189962. Both domains were designed to each contain engineered cysteine residues that permit formation of an intermolecular disulfide bond. This feature increases the stability of the fusion protein.

The amino acid sequence of the V$_H$-P38 Subunit (SEQ ID NO:1) of CAT-8015 is the following:

(SEQ ID NO: 1)
MEVQLVESGGGLVKPGGSLKLSCAASGFAFSIYDMSWVRQTPEKCLEWV

AYISSGGGTTYYPDTVKGRFTISRDNAKNTLYLQMSSLKSEDTAMYYCA

RHSGYGTHWGVLFAYWGQGTLVTVSA<u>KASGG</u>PEGGSLAALTAHQACHLP

LETFTRHRQPRGWEQLEQCGYPVQRLVALYLAARLSWNQVDQVIRNALA

SPGSGGDLGEAIREQPEQARLALTLAAAESERFVRQGTGNDEAGAANGP

ADSGDALLERNYPTGAEFLGDGGDVSFSTRGTQNWTVERLLQAHRQLEE

RGYVFVGYHGTFLEAAQSIVFGGVRARSQDLDAIWRGFYIAGDPALAYG

-continued

YAQDQEPDARGRIRNGALLRVYVPRSSLPGFYRTSLTLAAPEAAGEVER

LIGHPLPLRLDAITGPEEEGGRLETILGWPLAERTVVIPSAIPTDPRNV

GGDLDPSSIPDKEQAISALPDYASQPGKPPREDLK

The PE38 sequence is shown in bold, and the five amino acid linker between the $V_H$ domain and the PE38 domain is shown underlined.

The amino acid sequence of the $V_L$ Subunit (SEQ ID NO:2) of CAT-8015 is the following:

(SEQ ID NO: 2)
MDIQMTQTTSSLSASLGDRVTISCRASQDISNYLNWYQQKPDGTVKLLI

YYTSILHSGVPSRFSGSGSGTDYSLTISNLEQEDFATYFCQQGNTLPWT

FGCGTKLEIK

In further embodiments, the amino acid sequence of the VH domain of the immunoconjugate is one of the following:

(SEQ ID NO: 6)
MEVQLVESGGGLVKPGGSLKLSCAASGFAFSIYDMSWVRQTPEKCLEWV

AYISSGGGTTYYPDTVKGRFTISRDNAKNTLYLQMSSLKSEDTAMYYCA

RHSGYGTHWGVLFAYWGQGTLVTVSA (SEQ ID NO: 7)
MEVQLVESGGGLVKPGGSLKLSCAASGFAFSIYDMSWVRQTPEKCLEWV

AYISSGGGTTYYPDTVKGRFTISRDNAKNTLYLQMSSLKSEDTAMYYCA

RHSGYGYNWGVLFAYWGQGTLVTVSA (SEQ ID NO: 8)
MEVQLVESGGGLVKPGGSLKLSCAASGFAFSIYDMSWVRQTPEKCLEWV

AYISSGGGTTYYPDTVKGRFTISRDNAKNTLYLQMSSLKSEDTAMYYCA

RHSGYGTTWGVLFAYWGQGTLVTVSA (SEQ ID NO: 9)
MEVQLVESGGGLVKPGGSLKLSCAASGFAFSIYDMSWVRQTPEKCLEWV

AYISSGGGTTYYPDTVKGRFTISRDNAKNTLYLQMSSLKSEDTAMYYCA

RHSGYGSTYGVLFAYWGQGTLVTVSA (SEQ ID NO: 10)
MEVQLVESGGGLVKPGGSLKLSCAASGFAFSIYDMSWVRQTPEKCLEWV

AYISSGGGTTYYPDTVKGRFTISRDNAKNTLYLQMSSLKSEDTAMYYCA

RHSGYGTHWGVLFAYWGQGTLVTVSA (SEQ ID NO: 11)
MEVQLVESGGGLVKPGGSLKLSCAASGFAFSIYDMSWVRQTPEKCLEWV

AYISSGGGTTYYPDTVKGRFTISRDNAKNTLYLQMSSLKSEDTAMYYCA

RHSGYGSSYGVLFAYWGQGTLVTVSA

In additional embodiments, the amino acid sequence of the VL domain of the immunoconjugate is one of the following:

(SEQ ID NO: 12)
MDIQMTQTTSSLSASLGDRVTISCRASQDIARYLNWYQQKPDGTVKLLI

YYTSILHSGVPSRFSGSGSGTDYSLTISNLEQEDFATYFCQQGNTLPWT

FGCGTKLEIK (SEQ ID NO: 13)
MDIQMTQTTSSLSASLGDRVTISCRASQDIHGYLNWYQQKPDGTVKLLI

YYTSILHSGVPSRFSGSGSGTDYSLTISNLEQEDFATYFCQQGNTLPWT

FGCGTKLEIK (SEQ ID NO: 14)
MDIQMTQTTSSLSASLGDRVTISCRASQDIGRYLNWYQQKPDGTVKLLI

YYTSILHSGVPSRFSGSGSGTDYSLTISNLEQEDFATYFCQQGNTLPWT

FGCGTKLEIK (SEQ ID NO: 15)
MDIQMTQTTSSLSASLGDRVTISCRASQDIRGYLNWYQQKPDGTVKLLI

YYTSILHSGVPSRFSGSGSGTDYSLTISNLEQEDFATYFCQQGNTLPWT

FGCGTKLEIK

In certain other embodiments, the PE toxin of the immunoconjugate is a PE or variant thereof selected from the following:

Native PE
(SEQ ID NO: 16)
AEEAFDLWNECAKACVLDLKDGVRSSRMSVDPAIADTNGQGVLHYSMVL

EGGNDALKLAIDNALSITSDGLTIRLEGGVEPNKPVRYSYTRQARGSWS

LNWLVPIGHEKPSNIKVFIHELNAGNQLSHMSPIYTIEMGDELLAKLAR

DATFFVRAHESNEMQPTLAISHAGVSVVMAQTQPRREKRWSEWASGKVL

CLLDPLDGVYNYLAQQRCNLDDTWEGKIYRVLAGNPAKHDLDIKPTVIS

HRLHFPEGGSLAALTAHQACHLPLETFTRHRQPRGWEQLEQCGYPVQRL

VALYLAARLSWNQVDQVIRNALASPGSGGDLGEAIREQPEQARLALTLA

AAESERFVRQGTGNDEAGAANGPADSGDALLERNYPTGAEFLGDGGDVS

FSTRGTQNWTVERLLQAHRQLEERGYVFVGYHGTFLEAAQSIVFGGVRA

RSQDLDAIWRGFYIAGDPALAYGYAQDQEPDARGRIRNGALLRVYVPRS

SLPGFYRTSLTLAAPEAAGEVERLIGHPLPLRLDAITGPEEEGGRLETI

LGWPLAERTVVIPSAIPTDPRNVGGDLDPSSIPDKEQAISALPDYASQP

GKPPREDLK

PE40
(SEQ ID NO: 17)
GGSLAALTAHQACHLPLETFTRHRQPRGWEQLEQCGYPVQRLVALYLAAR

LSWNQVDQVIRNALASPGSGGDLGEAIREQPEQARLALTLAAAESERFVR

QGTGNDEAGAANADVVSLTCPVAAGECAGPADSGDALLERNYPTGAEFLG

DGGDVSFSTRGTQNWTVERLLQAHRQLEERGYVFVGYHGTFLEAAQSIVF

GGVRARSQDLDAIWRGFYIAGDPALAYGYAQDQEPDARGRIRNGALLRVY

VPRSSLPGFYRTSLTLAAPEAAGEVERLIGHPLPLRLDAITGPEEEGGRL

ETILGWPLAERTVVIPSAIPTDPRNVGGDLDPSSIPDKEQAISALPDYAS

QPGKPPREDLK

PE38
(SEQ ID NO: 18)
GGSLAALTAHQACHLPLETFTRHRQPRGWEQLEQCGYPVQRLVALYLAAR

LSWNQVDQVIRNALASPGSGGDLGEAIREQPEQARLALTLAAAESERFVR

QGTGNDEAGAANGPADSGDALLERNYPTGAEFLGDGGDVSFSTRGTQNWT

```
                                                        -continued
VERLLQAHRQLEERGYVFVGYHGTFLEAAQSIVEGGVRARSQDLDAIWRG

FYIAGDPALAYGYAQDQEPDARGRIRNGALLRVYVPRSSLPGFYRTSLTL

AAPEAAGEVERLIGHPLPLRLDAITGPEEEGGRLETILGWPLAERTVVIP

SAIPTDPRNVGGDLDPSSIPDKEQAISALPDYASQPGKPPREDLK

PE35
                                                    (SEQ ID NO: 19)
MWEQLEQCGYPVQRLVALYLAARLSWNQVDQVIRNALASPGSGGDLGEAI

REQPEQARLALTLAAAESERFVRQGTGNDEAGAANGPADSGDALLERNYP

TGAEFLGDGGDVSFSTRGTQNWTVERLLQAHRQLEERGYVFVGYHGTFLE

AAQSIVEGGVRARSQDLDAIWRGFYIAGDPALAYGYAQDQEPDARGRIRN

GALLRVYVPRSSLPGFYRTSLTLAAPEAAGEVERLIGHPLPLRLDAITGP

EEEGGRLETILGWPLAERTVVIPSAIPTDPRNVGGDLDPSSIPDKEQAIS

ALPDYASQPGKPPREDLK

PE-LR
                                                    (SEQ ID NO: 20)
RHRQPRGWEQLPTGAEFLGDGGDVSFSTRGTQNWTVERLLQAHRQLEERG

YVFVGYHGTFLEAAQSIVEGGVRARSQDLDAIWRGFYIAGDPALAYGYAQ

DQEPDARGRIRNGALLRVYVPRSSLPGFYRTSLTLAAPEAAGEVERLIGH

PLPLRLDAITGPEEEGGRLETILGWPLAERTVVIPSAIPTDPRNVGGDLD

PSSIPDKEQAISALPDYASQPGKPPREDLK

PE-LR-6X
                                                    (SEQ ID NO: 21)
RHRQPRGWEQLPTGAEFLGDGGDVSFSTRGTQNWTVERLLQAHRQLEEGG

YVFVGYHGTFLEAAQSIVEGGVRARSQDLDAIWAGFYIAGDPALAYGYAQ

DQEPDAAGRIRNGALLRVYVPRSSLPGFYATSLTLAAPEAAGEVERLIGH

PLPLRLDAITGPEEAGGRLETILGWPLAERTVVIPSAIPTDPRNVGGDLD

PSSIPDSEQAISALPDYASQPGKPPREDLK

PE-38 (CAT-8015)
                                                    (SEQ ID NO: 22)
PEGGSLAALTAHQACHLPLETFTRHRQPRGWEQLEQCGYPVQRLVALYLA

ARLSWNQVDQVIRNALASPGSGGDLGEAIREQPEQARLALTLAAAESERF

VRQGTGNDEAGAANGPADSGDALLERNYPTGAEFLGDGGDVSFSTRGTQN

WIVERLLQAHRQLEERGYVFVGYHGTFLEAAQSIVEGGVRARSQDLDAIW

RGFYIAGDPALAYGYAQDQEPDARGRIRNGALLRVYVPRSSLPGFYRTSL

TLAAPEAAGEVERLIGHPLPLRLDAITGPEEEGGRLETILGWPLAERTVV

IPSAIPTDPRNVGGDLDPSSIPDKEQAISALPDYASQPGKPPREDLK
```

The PE toxin of the immunoconjugate is fused or conjugated to either the VH or VL domain directly or via a linker at either the N-terminus or the C-terminus of the VH or VL domain. An example of a linker is described above for CAT-8015 and corresponds to the amino acid sequence KASGG (SEQ ID NO: 23). Additional linkers can be readily generated by techniques known in the art.

Expression of a PE Immunoconjugate

The PE immunoconjugate of the present invention is expressed in cells, such as bacterial cells, and then isolated from inclusion bodies. The PE immunoconjugate isolated from inclusion bodies is then further purified using downstream purification steps.

A variety of host-expression vector systems may be utilized to express the PE immunoconjugate of the present invention. Such host-expression systems represent vehicles by which the coding sequences of interest may be produced and subsequently purified, but also represent cells which may, when transformed or transfected with the appropriate nucleotide coding sequences, express an antibody molecule of the invention in situ. These include but are not limited to microorganisms such as bacteria (e.g., E. coli, B. subtilis) transformed with recombinant bacteriophage DNA, plasmid DNA or cosmid DNA expression vectors containing antibody coding sequences; yeast (e.g., Saccharomyces, Pichia) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors containing antibody coding sequences; or mammalian cell systems (e.g., COS, CHO, BLK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter).

DNA encoding each of the VL and VH-PE toxin (e.g., VH-PE38) polypeptides is introduced into an expression vector by techniques well known in the art.

A "vector" refers to any vehicle for the cloning of and/or transfer of a nucleic acid into a host cell. A vector may be a replicon to which another DNA segment may be attached so as to bring about the replication of the attached segment. A "replicon" refers to any genetic element (e.g., plasmid, phage, cosmid, chromosome, virus) that functions as an autonomous unit of DNA replication in vivo, i.e., capable of replication under its own control. The term "vector" includes vehicles for introducing the nucleic acid into a cell in vitro, ex vivo or in vivo. A large number of vectors known in the art may be used to manipulate nucleic acids, incorporate response elements and promoters, such as inducible promoters, into genes, etc. Possible vectors include, for example, plasmids such as pBR322 or pUC plasmid derivatives, or the Bluescript vector. For example, the insertion of the DNA fragments corresponding to response elements and promoters into a suitable vector can be accomplished by ligating the appropriate DNA fragments into a chosen vector that has complementary cohesive termini. Alternatively, the ends of the DNA molecules may be enzymatically modified or any site may be produced by ligating nucleotide sequences (linkers) into the DNA termini. Such vectors may be engineered to contain selectable marker genes that provide for the selection of cells. Such markers allow identification and/or selection of host cells that express the proteins encoded by the marker.

The term "expression vector" refers to a vector, plasmid or vehicle designed to enable the expression of an inserted nucleic acid sequence following transformation into the host. The cloned gene, i.e., the inserted nucleic acid sequence, e.g., a gene encoding an anti-CD22 VH, anti-CD22 VL, or anti-CD22 VH or VL fused to a PE toxin, is usually placed under the control of control elements such as a promoter, a minimal promoter, an enhancer, or the like. Initiation control regions or promoters, which are useful to drive expression of a nucleic acid in the desired host cell are numerous and familiar to those skilled in the art. Virtually any promoter capable of driving expression of these genes can be used in an expression vector, including but not limited to, viral promoters, bacterial promoters, animal promoters, mammalian promoters, synthetic promoters, constitutive promoters, tissue specific promoters, pathogenesis or disease related promoters, developmental specific promoters, inducible promoters, light regulated promoters; including, but are not limited to, the SV40 early (SV40) promoter region, the promoter contained in the 3' long terminal repeat (LTR) of Rous sarcoma virus (RSV), the E1A or major late promoter (MLP) of adenoviruses (Ad), the human cytomegalovirus (HCMV) immediate early promoter, the herpes simplex virus (HSV) thymidine kinase (TK) promoter, the baculovirus IE1 promoter, the elongation factor 1 alpha (EF1) promoter, the glyceraldehyde-3-phosphate dehydrogenase (GAPDH) promoter, the phosphoglycerate kinase (PGK) promoter, the ubiquitin C (Ube) promoter, the albumin promoter, the regulatory sequences of the mouse metallothionein-L promoter and transcriptional control regions, the ubiquitous promoters (HPRT, vimentin, β-actin, tubulin and the like), the promoters of the intermediate filaments (desmin, neurofilaments, keratin, GFAP, and the like), the promoters of therapeutic genes (of the MDR, CFTR or factor VIII type, and the like), pathogenesis or disease related-promoters. In addition, these expression sequences may be modified by addition of enhancer or regulatory sequences and the like.

The term "expression" refers to the biological production of a product encoded by a coding sequence. In most cases a DNA sequence, including the coding sequence, is transcribed to form a messenger-RNA (mRNA). The messenger-RNA is then translated to form a polypeptide product which has a relevant biological activity. Also, the process of expression may involve further processing steps to the RNA product of transcription, such as splicing to remove introns, and/or post-translational processing of a polypeptide product.

The VL and VH-PE38 polypeptides are expressed in cells, e.g., bacterial cells, such as E. coli. The polypeptides are expressed, e.g., in E. coli cells and isolated from inclusion bodies. In certain embodiments, the VL and VH-PE38 subunits are expressed in different cells. For example, the VL is expressed in one cell on a first vector and the VH-PE38 is expressed in a different cell on a second vector. Inclusion bodies from each cell line are recovered and solubilized. In certain embodiments, the inclusion bodies are solubilized at a pH in a range of about 9.0 to about 10.5. In further embodiments, the inclusion bodies are solubilized at a pH of 9.0, at a pH of 9.5, at a pH of 10.0 or a pH of 10.5. The solubilized VL and VH-PE38 inclusion bodies are combined to form an immunoconjugate comprising the VL and VH-PE38 subunits.

In other embodiments, the VL and VH-PE38 subunits are expressed in the same cell on different vectors, for example, the VL is expressed in one cell on a first vector, and the VH-PE38 is expressed in the same cell on a different vector. Inclusion bodies from the cell are recovered, solubilized and the VL and VH-PE38 subunits combined to form an immunoconjugate. In certain other embodiments, the VL and VH-PE38 subunits are expressed on the same vector in the same cell.

Downstream chromatography steps are utilized to further purify this immunoconjugate.

Chromatography Conditions

As appreciated in the art, load, wash, and elution conditions for use in the chromatography of the invention will depend on the specific chromatography media/ligands used. The process of the invention can, of course, be used in combination with other protein purification methodologies, such as salt precipitation, affinity chromatography, hydroxyapatite chromatography, reverse phase liquid chromatography, or any other commonly used protein purification technique. It is contemplated, however, that the process of the present invention will eliminate or significantly reduce the need for other purification steps.

Anionic exchange chromatography is also performed during chromatographic separation of the polypeptide of interest. As is well known in the art, anion exchangers may be based on various materials with respect to the matrix as well as to the attached charged groups. For example, the following matrices may be used, in which the materials mentioned may be more or less cross-linked: agarose based (such as SEPHAROSE Fast Flow® (such as Q-SEPHAROSE FF), and SEPHAROSE High Performance®; cellulose based (such as DEAE SEPHACEL®); silica based and synthetic polymer based, or resins such as SuperQ-650 (from TOSOH BIOSEP) and Macro High Q (from BIO-RAD). For the anion exchange resin, the charged groups which are covalently attached to the matrix may, e.g., be diethylaminoethyl (DEAE), quaternary aminoethyl (QAE), and/or quaternary ammonium (Q). In certain embodiments, the resin is selected from the group including, but not limited to, Q Sepharose High Performance, Q Sepharose Fast Flow, DEAE Sepharose Fast Flow, Capto Q, Capto DEAE, Toyopearls SuperQ 650 (M), Toyopearls SuperQ 650 (S), Toyopearls DEAE 650 (M), Toyopearls DEAE 650 (S), TSKgel SuperQ-5PW (30), TSKgel SuperQ-5PW (20), TSKgel DEAE-5PW (30), TSKgel DEAE-5PW (20), EMD Chemicals: Fractogel EMD DEAE (S), Fractogel EMD DEAE (M), Fractogel EMD DMAE (S), Fractogel EMD DMAE (M), Fractogel EMD TMAE (S), Fractogel EMD TMAE (M), and Baker Bond XWP500 PolyQuat-35, SPE. In one embodiment of the present process, the anion exchange resin employed is Q-SEPHAROSE FF®.

Although any of these resins may be used for small scale purification of antibodies, resins of certain size and lower cost are amenable to manufacturing scale separation. If the size of the resin is too small, there is considerable back pressure generated in the system. In addition, the amount of polypeptide that can be purified is limited. If the resin is costly to make or purchase, it is not economically feasible/practical for use in large scale purification.

Thus, the resin used in the present invention must be of a certain size to provide efficient scale-up without being prohibitively expensive. "Manufacturing level purification" means purification of antibodies from a recombinant preparation on a scale that meets commercial scale production. The resin used in the predetermination step should be the same as that used in the final protocol for manufacturing level purification because one may not easily predict the variation in conditions necessary to separate the aggregates if the resin is changed. A particular resin that is useful in small scale or bench top purification may not be amenable to large scale purification. Such resins useful for the present invention include, e.g., Q-SEPHAROSE HP. However, the skilled artisan would recognize other anion exchange resins useful for commercial scale production.

The volume of resin used when packing an anion exchange chromatography column is reflected by the dimensions of the column, i.e., the diameter of the column and the height of the resin, and varies depending on, e.g., the amount of antibody in the applied solution and the binding capacity of the resin used.

Before performing an anion exchange chromatography, the exchange resin may be equilibrated with a buffer. Any of a variety of buffers are suitable for the equilibration of exchange resin, e.g., sodium acetate, sodium phosphate, TRIS(hydroxymethyl) amino-methane, TRIS, phosphate, bis-TRIS, and L-histidine. Persons skilled in the art will appreciate that numerous other buffers may be used for the equilibration as long as the pH and conductivity are about the same as for the applied antibody solution. When performing the "bind-washout" process, the equilibration buffers and the wash buffers are the same. When performing the "bind-elute" process, the elution buffers may be made of one or more buffer substances to control the pH. The salt used is, e.g., a highly soluble salt, such as sodium chloride or potassium phosphate, but any salt may be used that maintains the functionality of the antibody and allows removal of the antibody monomer from the resin.

In performing the "bind-elute" process, the elution of the antibody monomers from the resin may be performed with a substantially non-denaturing buffer having a pH and ionic strength sufficient to efficiently elute the monomeric antibody, thereby recovering an antibody-containing eluate, while leaving the aggregates bound to the resin. In this context, efficient elution means that at least 75%, or at least 80%, or at least 85%, or at least 90%, or at least 95% of the antibody loaded onto the resin is recovered. Only about 1.0%, preferably only 0.5%, most preferably less than 0.1% aggregates remain in the antibody preparation following ion exchange.

In one embodiment, the elution is carried out as a step gradient elution. In another embodiment, the elution is carried out in a linear gradient.

Surprisingly, deamidated variants of the immunoconjugate proteins eluted at higher salt concentration despite the apparent net increase of negative charge due to deamidation of an asparagine residue. Therefore, these reduced potency variants were separated from the more active proteins by the ion exchange chromatography described herein.

In certain embodiments of the invention, about 75% to about 99% of the acidic or deamidated variant present within the starting sample of the polypeptide or immunoconjugate is removed during the purification process. In other embodiments, at least 75%, 80%, 85%, 90%, 95%, 97%, 98% or 99% of the deamidated variant is removed. The composition comprising the active polypeptide or immunoconjugate thus has less than between about 25% and about 1% deamidated species, for example, less than 25%, less than 20%, less than 15%, less than 10%, less than 5%, less than 4%, less than 3%, less than 2% or less than 1%.

Deamidated variants of the invention include immunoconjugates comprising a PE toxin or variant thereof, wherein the deamidation occurs at one or more residues within the immunoconjugate, for example, at one or more residues within the PE toxin or variant thereof. In certain embodiments, deamidation occurs at 1, 2 3, 4 or 5 residues within the immunoconjugate. In other embodiments, an immunoconjugate comprising a PE toxin or variant thereof is deamidated at 1, 2, 3, 4, or 5 residues within the PE toxin or variant thereof, for example at position 358 of SEQ ID NO:1, at position 495 of SEQ ID NO: 16, at position 243 of SEQ ID NO:17, at position 227 of SEQ ID NO:18, at position 200 of SEQ ID NO:19, at position 212 of SEQ ID NO: 20, at position 212 of SEQ ID NO: 21 or at position 229 of SEQ ID NO: 22.

In one embodiment, the salt concentration of the eluting buffer is sufficiently high to displace the antibody monomers from the resin without displacing the aggregates. However, it is contemplated that an increase in pH and a lower salt concentration can be used to elute the antibody monomers from the resin.

Any or all chromatographic steps of the present invention can be carried out by any mechanical means. Chromatography may be carried out, for example, in a column. The column may be run with or without pressure and from top to bottom or bottom to top. The direction of the flow of fluid in the column may be reversed during the chromatography process. Chromatography may also be carried out using a batch process in which the solid media is separated from the liquid used to load, wash, and elute the sample by any suitable means, including gravity, centrifugation, or filtration. Chromatography may also be carried out by contacting the sample with a filter that absorbs or retains some molecules in the sample more strongly than others. In the following description, the various embodiments of the present invention are described in the context of chromatography carried out in a column. It is understood, however, that use of a column is merely one of several chromatographic modalities that may be used, and the illustration of the present invention using a column does not limit the application of the present invention to column chromatography, as those skilled in the art may readily apply the teachings to other modalities as well, such as those using a batch process or filter.

A variety of different loading, washing and elution conditions can be used, as desired. In some embodiments, the initial loading conditions are adapted such that the protein (e.g., antibody) eluted from the initial non-HT is applied directly to the HT column.

Elution can be achieved, for example, by changing the salt conditions in the liquid phase. For example, the salt and/or conductivity of the liquid phase is increased (linearly or step-wise) to a point that which the antibody elutes. Exemplary washing conditions include, e.g., 10 mM phosphate, pH 6.7, with elution achieved by increasing the salt concentration (step-wise or in a linear fashion) (e.g., to 10 mM phosphate, 1.5M NaCl, pH 6.7). All of the various embodiments or options described herein can be combined in any and all variations.

Before the sample is applied to the column, the column can be equilibrated in the buffer or salt that will be used to chromatograph the protein. As discussed below, chromatography (and loading of the protein to be purified) can occur in a variety of buffers or salts including sodium, potassium, ammonium, magnesium, calcium, chloride, fluoride, acetate, phosphate, and/or citrate salts and/or Tris buffer. Citrate buffers and salts are preferred by those skilled in the art for their ease of disposal. Such buffers or salts can have a pH of at least about 5.5. In some embodiments, equilibration may take place in a solution comprising a Tris or a sodium phosphate buffer. In some embodiments, equilibration takes place at a pH of at least about 5.5. Equilibration may take place at pHs between about 6.0 and about 8.6, preferably at pHs between about 6.5 and 7.5. Most preferably, the solution comprises a sodium phosphate buffer at a concentration of about 25 millimolar and at a pH of about 6.8.

The protein purification process of the present invention is applicable to removal of an acidic variant from any protein. Some proteins specifically contemplated for use with the invention include antibodies or fragments thereof. Other proteins include, but are not limited to recombinant fusion proteins comprising one or more constant antibody immunoglobulin domains, optionally an Fc portion of an antibody, and a protein or interest.

Formulations

Formulations of the purified polypeptides or immunoconjugates are prepared for storage and use by combining a purified polypeptide or immunoconjugate of the present invention with a pharmaceutically acceptable vehicle (e.g., carrier, excipient) (Remington, The Science and Practice of Pharmacy 20th Edition Mack Publishing, 2000). Suitable pharmaceutically acceptable vehicles include, but are not limited to, nontoxic buffers such as phosphate, citrate, and other organic acids; salts such as sodium chloride; antioxidants including ascorbic acid and methionine; preservatives (e.g., octadecyldimethylbenzyl ammonium chloride; hexamethonium chloride; benzalkonium chloride; benzethonium chloride; phenol, butyl or benzyl alcohol; alkyl parabens, such as methyl or propyl paraben; catechol; resorcinol; cyclohexanol; 3-pentanol; and m-cresol); low molecular weight polypeptides (e.g., less than about 10 amino acid residues); proteins such as serum albumin, gelatin, or immunoglobulins; hydrophilic polymers such as polyvinylpyrrolidone; amino acids such as glycine, glutamine, asparagine, histidine, arginine, or lysine; carbohydrates such as monosaccharides, disaccharides, glucose, mannose, or dextrins; chelating agents such as EDTA; sugars such as sucrose, mannitol, trehalose or sorbitol; salt-forming counter-ions such as sodium; metal complexes (e.g., Zn-protein complexes); and non-ionic surfactants such as TWEEN or polyethylene glycol (PEG).

The antibody and/or immunoconjugate compositions of this invention (i.e., PE linked to an antibody), are particularly useful for parenteral administration, such as intravenous administration or administration into a body cavity or lumen of an organ. The compositions for administration will commonly comprise a solution of the antibody and/or immunoconjugate dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of fusion protein in these formulations can vary widely, and will be selected primarily based on fluid volumes, viscosities, body weight and the like in accordance with the particular mode of administration selected and the patient's needs.

Thus, a typical pharmaceutical immunoconjugate composition for intravenous administration would be at a total treatment of about 0.3 to about 50 µg/kg per day, in particular 20-50 µg/kg per day with the dosage preferably administered continuously or allocated at three times per day. Actual methods for preparing administrable compositions will be known or apparent to those skilled in the art and are described in more detail in such publications as Remington's Pharmaceutical Science, 19th ed., Mack Publishing Company, Easton, Pa. (1995).

The composition including the present invention's immunoconjugate can be administered for therapeutic treatments. In therapeutic applications, compositions are administered to a patient suffering from a disease, in an amount sufficient to cure or at least partially arrest the disease and its complications. An amount adequate to accomplish this is defined as a "therapeutically effective dose." Amounts effective for this use will depend upon the severity of the disease and the general state of the patient's health.

Single or multiple administrations of the compositions may be administered depending on the dosage and frequency as required and tolerated by the patient. In any event, the composition should provide a sufficient quantity of the proteins of this invention to effectively treat the patient. The dosage can be administered three times a day every other day or continuously every other day for a cycle of, e.g., 21 days, but may be applied periodically until either a therapeutic result is achieved or until side effects warrant discontinuation of therapy. Generally, the dose should be sufficient to treat or ameliorate symptoms or signs of disease without producing unacceptable toxicity to the patient. An effective amount of the compound is that which provides either subjective relief of a symptom(s) or an objectively identifiable improvement as noted by the clinician or other qualified observer.

In one embodiment, the immunoconjugate is formulated as a pharmaceutical composition comprising at least one acceptable excipient. Pharmaceutically acceptable CAT-8015 immunoconjugate formulations include 0.5 mg/mL to 2.5 mg/mL CAT-8015, usually 1.0 mg/mL, 1.1 mg/mL, 1.2 mg mL, 1.3 mg/mL, 1.4 mg/mL or 1.5 mg/mL in 25 mM sodium phosphate, 4% sucrose, 8% glycine, 0.02% polysorbate 80 (PS80), pH 7.4. In additional embodiments, the sodium phosphate can be in a range of 20 mM to 100 mM, 25 mM to 50 mM, or 25 mM to 35 mM; the sucrose can be at 2%, 3%, 4%, 5% or 6%; the glycine can be in the range of 5-10%, usually, 5%, 6%, or 7%; the polysorbate 80 can be in a range from about 0.01% to about 1%, usually 0.01%, 0.02%, 0.03%, 0.04% or 0.05%; with a pH in the range of 6.5 to 8.0, usually at pH 7.2, 7.3, 7.4, 7.5 or 7.6. Other buffering agents known to one of ordinary skill in the art can also be utilized.

In certain embodiments of the invention, the formulation is lyophilized. The term "lyophilized" refers to any composition or formulation that is prepared in dry form by rapid freezing and dehydration, in the frozen state under high vacuum. "Lyophilizing" or "lyophilization" refers to a process of freezing and drying a solution. Lyophilized formulations or compositions are often made ready for use or reconstituted by addition of sterile distilled water. In certain embodiments, the lyophilized formulation of the invention is reconstituted into a vial.

For intravenous administration, a formulation of the invention, such as a liquid formulation or a formulation reconstituted from a lyophilized formulation is placed in a vial where the immunoconjugate in the formulation is present at concentrations as described above. This formulation is extracted from the vial and added to an intravenous (IV) bag solution, where the IV bag contains from about 30 mL to about 100 mL solution, usually 50 mL, 60 mL, 70 mL or 80 mL. A separate IV bag "protectant solution" can also be added to the total volume of the IV bag where the protectant solution contains polysorbate 80 in an amount such that the polysorbate 80 present in the final IV bag solution is in a range of 0.001% to about 3% polysorbate 80, usually in the range of about 0.01% to about 0.1%, and more usually at 0.01%, 0.02%, 0.03%, 0.04% or 0.05%. The protectant solution can be pre-formulated in a vial such that the polysorbate 80 is at a concentration of about 0.5% to about 5%, and can be 0.5%, 1.0%, 1.5%, 2.0%, 2.5%, 3.0%, 3.5%, 4.0%, 4.5% or 5.0% The protectant solution prevents adsorption of the immunoconjugate or drug (e.g., CAT-8015) to contact surfaces of the IV bag, thereby preventing or inhibiting the immunoconjugate or drug from sticking to the IV bag during administration and allowing the patient to receive the appropriate dosage of immunoconjugate or drug. The IV bag solution can be administered by infusion to the patient for various durations, usually 30 minutes to 1 hour, usually 30 minutes.

Among various uses of the immunoconjugates and formulations of the present invention are included a variety of disease conditions caused by specific human cells that may be eliminated by the toxic action of the protein. One application for the immunoconjugates of the invention is for the treatment of B cell malignancies or malignant B cells expressing CD22. Exemplary B cell malignancies include chronic B-lymphocytic cells (B-CLL), pediatric acute lyphocytic leukemia (pALL), follicular lymphoma (FL), diffuse large B cell lymphoma (DLBCL), Non Hodgkins lymphoma (NHL) and hairy cell leukemia (HCL).

All documents, patents, journal articles and other materials cited in the present application are hereby incorporated by reference.

Although the present invention has been fully described in conjunction with several embodiments thereof with reference to the accompanying drawings, it is to be understood that various changes and modifications may be apparent to those skilled in the art. Such changes and modifications are to be understood as included within the scope of the present invention as defined by the appended claims, unless they depart therefrom.

EXAMPLES

Example 1

Expression, Recovery and Inclusion Body Isolation of CAT-8015

Fermentation of separate cell lines containing CAT-8015 VL and CAT-8015 VH-PE38 expression vectors was performed. The fermentor was harvested by continuous centrifugation. The fermentor harvest was passed through a continuous centrifuge at 2 to 8° C. at a rate of 0.5 to 0.8 L per minute and centrifuged at a speed of approximately 15,000 rpm. After centrifugation the cell paste was frozen at ≤−70° C.

Following this treatment, the VH-PE38 and VL cell pastes were thawed for 12 to 24 hours at 2 to 8° C. The cells were lysed to release inclusion bodies containing the VL and VH-PE38 products. The resulting inclusion bodies were subsequently solubilized and the VH-PE38 and VL products obtained.

The product was concentrated to approximately 1 mg/mL (determined by Coomassie total protein assay) using a 30 kDa ultrafiltration hollow fiber cartridge. The retentate was then diafiltered with 5 to 6 volumes of 20 mM Tris, 100 mM urea pH 7.4 to achieve a conductivity of 2.5 to 3.0 mS/cm. This product was stored up to 72 hours at 2 to 8° C.

Example 2

Analytical-Scale Purification of Active CAT-8015 by Anion Exchange Chromatography with High Performance Resins Expression of the $V_H$-P38 subunit resulted in a formation of a deamidated variant of the subunit. The deamidation was found to occur in the PE38 portion of the immunoconjugate. Deamidation of the $V_H$-P38 subunit resulted in decreased potency of the CAT-8015 protein. Surprisingly, the below described chromatographic conditions were successful in removing the deamidated variant, thus providing the ability to remove the inactive species during purification. Since the deamidation occurred in the PE38 portion of the fusion construct, the chromatographic conditions can be applied to removal of any deamidated variant of a PE conjugate.

CAT-8015 was renatured from isolated inclusion bodies and subsequently purified by a 4-column process. Table 1 provides an overview of the renaturation and purification unit operations.

TABLE 1

| CAT-8015 production | |
|---|---|
| Step | Unit Operation |
| 1 | Fermentation |
| 2 | Primary Recovery |
| 3 | Inclusion Body Isolation |
| 4 | Refold |
| 5 | Capture Step |
| 6 | Intermediate Purification Step I |
| 7 | Intermediate Purification Step II |
| 8 | Anion Exchange Chromatography |
| 9 | Formulation (Drug Substance) |

FIG. 1 shows the analytical ion exchange chromatography (IEC) profile of a sample of a CAT-8015 reference standard. As shown in the profile, a pre-peak emerges prior to the elution of the main peak. The individual fractions eluted from the IEC are assayed for CAT-8015 biological activity relative to a reference standard using an apoptosis bioassay that measures the ability of the test sample to induce dose dependent apoptotic death of the CD22 receptor-expressing Daudi cell line. Once bound to CD22 and internalized, CAT-8015 induces Daudi cells to undergo apoptosis via Caspase 3/7 activation that can be measured by Caspase-Glo™ 3/7 Assay System. The potency of the test sample is determined by dividing the 50% effective concentration (EC50) of the Reference Standard by the EC50 of the test sample. The results of the apoptosis bioassay demonstrated that the relative potency of CAT-8015 is correlated with the percentage of pre-peak of CAT-8015 as diagrammed in FIG. 1. FIG. 2 shows the correlation between this relative potency and the percentage of pre-peak.

Pre-peak and main peak fractions from multiple IEC analysis were collected, pooled and subjected to peptide mapping and liquid chromatography-mass spectrometry/mass spectrometry (LC-MS/MS) analysis. Results were compared to those obtained from peptide mapping and LC-MS/MS experiments of purified CAT-8015. The analysis of purified CAT-8015 drug substance revealed that Asn-358 was partially deamidated to Asp-358 and iso-Asp-358 (Table 2). Asp-358 and iso-Asp358 were found to be significantly enriched in the pre-peak fraction whereas the main peak fraction was enriched in intact CAT-8015 (Table 2). Taken together, the results demonstrate that deamidation at Asn-358 lead to a loss of relative potency in a cell based bioassay. The Asp-358 residue is present within the PE toxin portion of the immunoconjugate thus indicating that an immunoconjugate containing a PE toxin, or variant thereof, in which Asp-358 is present will likely be subject to deamidation and subject to a loss of potency or activity.

TABLE 2

Distribution of Amino Acid 358 in CAT-8015 Drug Substance, Pre-Peak and Main Peak Fractions based on Peptide Mapping and LC-MS/MS Analysis.

| Amino Acid | Drug Substance (%) | Pre-Peak (%) | Main Peak (%) |
|---|---|---|---|
| N358 | 78.1 | 3.1 | 88.9 |
| D358 | 11.9 | 44.0 | 2.2 |
| iso-D358 | 10.0 | 52.9 | 8.9 |

D358 = deamidated Asn-358; iso-D358 = iso-deamidated Asn-358; N358 = Asn-358.

Separation of deamidated CAT-8015 from intact CAT-8015 was achieved by anion exchange chromatography with strong ion exchange groups such as Q (quaternary amino) coupled to small diameter resins such as Source 15 (particle diameter: 15 μm; GE Healthcare) and Sepharose High Performance (particle diameter: 34 μm; GE Healthcare). The application of small diameter chromatography resin in biomanufacturing processes is complicated by the generation of significant back pressures under typical operating conditions as defined by column geometry, flow rates and buffer composition. Based on these considerations and the requirement for a high resolution chromatography step Q Sepharose High Performance was chosen for the separation of deamidated CAT-8015 from intact CAT-8015. Chromatography conditions were developed that achieved high resolution while maintaining operability at various manufacturing scales.

Example 3

Bench-Scale Purification of CAT-8015

The column was first pre-equilibrated with 5 column volumes (CVs) of Buffer C (Pre-Equilibration/Stripping Buffer: 10 mM Tris/HCl, pH 8.0, 1.0M NaCl) and subsequently equilibrated with 5 CVs Buffer A (Equilibration Buffer: 10 mM Tris/HCl, pH 8.0) at a linear flow rate of 100 cm/hr. The chromatography resin was Q Sepharose High Performance (QHP, GE Healthcare) in a Millipore Vantage column, 2.2 cm×19.5 cm, and run on an AKTA Explorer. The intermediate purification product pool was prepared for loading onto the high performance anion exchange column by diafiltration with 10 volumes of Buffer A using a 10 kDa MWCO membrane. The diafiltered hydrophobic interaction product pool was loaded onto the QHP column at a linear flow rate of 100 cm/hr, followed by a 2 CV re-equilibration step with Buffer A at the same flow rate. CAT-8015 was eluted with a 10 CV linear gradient from 35% Buffer B (Elution Buffer: 10 mM Tris/HCl, pH 8.0, 500 mM NaCl) to 55% Buffer B at a linear flow rate of 100 cm/hr. Elution of product was monitored at 280 nm. Fractions were collected and analyzed for % pre-peak by analytical ion exchange chromatography (IEC). Fractions containing less than 25% pre-peak were pooled. The QHP pool was analyzed for % pre-peak by analytical IEC on a strong anion exchange column. Relative potency was measured by an apoptosis bioassay as described above.

At pH 8.0, CAT-8015 strongly bound to the anion exchange resin with no protein detected in the flow-through fraction by absorbance at A280. After an initial wash step with 175 mM NaCl in Tris/HCl, pH 8.0, CAT-8015 was eluted from the column with a linear salt gradient from 35% B (175 mM NaCl in Tris/HCl, pH 8.0) to 55% B (275 mM NaCl in Tris/HCl, pH 8.0). CAT-8015 eluted from the column between 39% B (192 mM NaCl in Tris/HCl, pH 8.0) and 49% B (245 mM NaCl in Tris/HCl, pH 8.0). FIG. 3 shows the QHP chromatography profile of CAT-8015.

Fractions were analyzed by analytical IEC. Table 3 shows the results for fractions eluted between 44.5% B (223 mM NaCl) and 47.2% B (236 mM NaCl).

TABLE 3

IEC Analysis of Collected QHP Fractions

| Fraction No. | % Pre-Peak[a] | % Main Peak |
|---|---|---|
| C12 | 41.0 | 59 |
| D12 | 34.5 | 65.5 |
| D11 | 27.0 | 73 |
| D9 | 17.6 | 82.4 |
| D7 | 15.9 | 84.1 |
| D5 | 18.7 | 81.3 |
| D3 | 21.9 | 78.1 |

[a]Pre-peak contains >90% deamidated CAT-8015.

Table 3 demonstrates that anion exchange chromatography operated in a linear salt gradient elution mode is able to separate deamidated CAT-8015 from intact CAT 8015 in an effective manner.

Surprisingly, intact CAT-8015 was eluted at a higher salt concentration despite the apparent net increase of negative charge due to deamidation of an asparagine residue. This result is consistent with the chromatography profile observed by IEC. CAT-8015-containing samples were injected on an analytical anion exchange column (PL-SAX, Varian) equilibrated at pH 8.0 with a Tris/HCl buffer system and eluted by a combination of step and gradient elution steps (FIG. 1).

Fractions were combined according to the pooling criteria of less than 25% pre-peak content. The QHP pool was analyzed for % pre-peak and relative potency by SDS-PAGE, analytical IEC and apoptosis bioassay. The SDS-PAGE analysis, as shown in FIG. 4, demonstrates that QHP load pool and eluate samples contained highly purified CAT-8015. However, the QHP load pool did not meet target specification for purity by IEC and bioactivity. Purity and potency measurements for the QHP load pool as compared to the QHP eluate pool, as presented in Table 4 below, demonstrate that the anion exchange chromatography step with QHP resulted in a significant increase in purity by IEC and relative potency of CAT-8015. The QHP load pool was generated from Intermediate Purification Step II.

TABLE 4

CAT-8015 Purity by IEC and Bioactivity

| Step | % Pre-Peak | % Main Peak | Relative Potency (%) |
|---|---|---|---|
| QHP Load Pool | 53.8 | 46.2 | 52 |
| QHP Eluate Pool | 16.5 | 83.8 | 80 |

The QHP product pool was subsequently diafiltered into formulation buffer to generate CAT-8015 drug substance.

Thus, the manufacture of CAT-8015 drug substance requires the separation of deamidated CAT-8015 from active CAT-8015. The capability of anion exchange chromatography with high performance resins such as QHP to separate deamidated CAT-8015 from intact CAT-8015 and to increase bioactivity to target specifications is a prerequisite for the successful manufacture of CAT-8015 drug substance.

Example 4

Large-Scale Purification of CAT-8015

The column was first pre-equilibrated with 5 CVs Buffer C (Pre-Equilibration/Stripping Buffer: 10 mM Tris/HCl, pH 8.0, 1.0M NaCl) at a linear flow rate of 66 cm/hr and subsequently equilibrated with 5 CVs Buffer A at a linear flow rate of 76 cm. The chromatography resin was Q Sepharose High Performance (QHP, GE Healthcare), in a BP300, 30 cm×22 cm column bed, run on a K Prime instrument. The intermediate purification product pool was prepared for loading onto the high performance anion exchange column by diafiltration with 10 volumes of Buffer A (Equilibration Buffer: 10 mM Tris/HCl, pH 8.0) using a 10 kDa MWCO membrane. The diafiltered product pool was loaded onto the QHP column at a linear flow rate of 64 cm/hr, followed by a 2 CV re-equilibration step with Buffer A at 76 cm/hr. CAT-8015 was eluted with a 10 CV linear gradient from 35% Buffer B (Elution Buffer: 10 mM Tris/HCl, pH 8.0, 500 mM NaCl) to 55% Buffer B at a linear flow rate of 76 cm/hr. Elution of product was monitored at 280 nm. Fractions were collected and analyzed for % pre-peak by analytical ion exchange chromatography (IEC). Fractions containing less than 25% pre-peak were pooled. The QHP pool was analyzed for % pre-peak by analytical IEC on a strong anion exchange column. Relative potency was measured by an apoptosis bioassay.

Large scale anion exchange chromatography of CAT-8015 with QHP was performed as described above. QHP purification was carried out at reduced flow rates due to equipment constraints. CAT-8015 eluted from the column at conductivities between 22.3 mS/cm and 26.4 mS/cm. FIG. 5 shows the QHP chromatography profile of CAT-8015 purified according to the method described above.

Fractions were analyzed by analytical IEC. Table 5 shows the results for fractions eluted at conductivities between 23.8 and 25.4 mS/cm. Table 5 demonstrates that anion exchange chromatography operated in a linear salt gradient elution mode was able to separate deamidated CAT-8015 from intact CAT 8015. Separation of deamidated CAT-8015 from intact CAT-8015 took place within a conductivity range of less than 2 mS/cm.

TABLE 5

IEC Analysis of Collected Fractions % Pre-peak purity

| Fraction | % Pre-Peak | % Main Peak |
|---|---|---|
| 1 | 55.1 | 44.9 |
| 2 | 39.0 | 61 |
| 3 | 30.1 | 69.9 |
| 4 | 25.1 | 74.9 |
| 5 | 18.7 | 81.3 |
| 6 | 14.7 | 85.3 |
| 7 | 16.4 | 83.6 |

Fractions 4-7 were combined according to the pooling criteria of less than 25% pre-peak content. The QHP pool was analyzed for % pre-peak and relative potency by SDS-PAGE and SEC, analytical IEC and apoptosis bioassay. The SDS-PAGE analysis, as shown in FIG. 6, demonstrates that QHP load pool and eluate samples contained highly purified CAT-8015. However, the QHP load pool did not meet target specification for purity by SEC, IEC and relative potency. Purity and potency measurements for the QHP load pool as compared to the QHP eluate pool, as presented in Tables 6 and 7 below, demonstrate that the anion exchange chromatography step with QHP resulted in a significant increase in purity by SEC, IEC and relative potency of CAT-8015. The QHP load pool was generated from Intermediate Purification Step II.

TABLE 6

CAT-8015 Purity by SEC

| Step | % Monomer | % Aggregate | % Other |
|---|---|---|---|
| QHP Load Pool | 92.7 | 0.7 | 6.6 |
| QHP Eluate Pool | 99.0 | 1.0 | 0 |

TABLE 7

CAT-8015 Purity by IEC and Bioactivity

| Step | % Pre-Peak | % Main Peak | Relative Potency (%) |
|---|---|---|---|
| QHP Load Pool | 50.3 | 49.7 | 51 |
| QHP Eluate Pool | 17 | 83 | 75 |

The QHP product pool was subsequently diafiltered into formulation buffer to generate CAT-8015 drug substance.

Examples 2-4 demonstrate the capacity of anion exchange chromatography with resins such as Q Sepharose High Performance to separate deamidated CAT-8015 from intact CAT-8015 and to increase its relative potency to meet target specifications (see Tables 4 and 6). Deamidated CAT-8015 differs from intact CAT-8015 by one additional negative charge. In contrast to the expected elution behavior from an anion exchange column, the bulk of deamidated CAT-8015 elutes prior to intact CAT-8015 under salt gradient elution conditions (see Tables 3 and 5). This unexpected elution pattern was observed at analytical scale, bench scale, and large scale anion exchange chromatography. This elution pattern was unexpected as the linear high salt elution buffer would be expected to result in a higher negative charge of the variant. Thus, Examples 2-4 demonstrate that using a linear elution buffer, a deamidated species can be removed from active immunoconjugates using anion-exchange chromatography. Separation of deamidated CAT-8015 from intact CAT-8015 took place within a particular range of conductivities, underscoring the need for high resolution anion exchange resins, careful control of elution conditions and in-process testing of collected fractions.

Example 5

Modifying the Bioactivity of CAT-8015 Formulations

The potency of CAT-8015 compositions was calibrated by mixing specific quantities of the deamidated pre-peak with the active main peak. To obtain compositions comprising a particular potency of CAT-8015, aliquots of CAT-8015 pre-peak product were combined with aliquots of CAT-8015 main peak product to achieve a composition with a particular potency of CAT-8015. By controlling the level of CAT-8015 potency in the composition, a CAT-8015 formulation was generated for administration of a particular volume of reconstituted CAT-8015 at a desired dose.

Example 6

Adjusting pH During Solubilization Results in Reduced Deamidation Species as Measured after Capture and Intermediate Purification Steps While deamidated species can be removed from active immunoconjugates using the purification steps as described above, levels of deamidated species of CAT-8015 can also be effectively reduced by adjusting the pH at earlier steps in the purification process (i.e., the refold step (Step 4 of Table 1 above). The refold procedure utilized to achieve a lower level of deamidated species of CAT-8015 includes the following substeps:

Refold Substep 1: Solubilization, Clarification and Concentration:

VH-PE38 and VL inclusion bodies were thawed for 12-24 hours at room temperature (15-30° C.). VH-PE38 and VL inclusion bodies were combined in a 1:1 molar ratio and adjusted to 15% (w/v) solids by adding 50 mM Tris, 20 mM EDTA, pH 7.4. The inclusion bodies were solubilized by adding 5 kg of inclusion body solubilization buffer (50 mM ethanolamine, 8 M urea, 0.5 M arginine, 2 mM EDTA, 10 mM DTE) for each kg of 15% (w/v) solids inclusion body suspension. The pH of the inclusion body solubilization buffer was varied between pH 9.0 and 10.5 in 0.5 pH unit increments. Solubilization was carried out for 2 hours at room temperature (15-30° C.) with constant stirring. Solubilized inclusion bodies were clarified by depth filtration through a series of filters. The clarified filtrate was concentrated by tangential flow filtration to 5-6 g/L using a 5 kDa molecular weight cutoff (MWCO) ultra filtration membrane.

Refold Substep 2: Refold:

The refolding of CAT-8015 was initiated by a 10-fold dilution of the clarified and concentrated inclusion body filtrate into pre-chilled (2-8° C.) refolding buffer (50 mM ethanolamine, 1 M arginine, 2 mM EDTA, 0.91 mM oxidized glutathione, pH 9.5). The refold solution was maintained at 2-8° C. for 48-72 hours with continuous mixing. The refold was terminated by bringing the refold solution to room temperature (15-30° C.) prior to concentration and diafiltration. The refold solution was concentrated by tangential flow filtration with a 10 kDa MWCO membrane, and diafiltered with 10 volumes of 20 mM potassium phosphate, pH 7.4. The concentrated and diafiltered refold solution was filtered through a 0.2 μm filter (TMAE load).

As part of the capture step (Step 5 of Table 1 above), the CAT-8015 preparation obtained from the refold procedure above was loaded onto a Fractogel TMAE column (EMD Biosciences or equivalent) equilibrated with 20 mM potassium phosphate, pH 7.4. After loading, the column was first washed with 20 mM potassium phosphate, pH 7.4, and then with 20 mM potassium phosphate, 0.1% (w/w) Triton X 100, pH 7.4, followed by a subsequent wash with 20 mM potassium phosphate, 100 mM sodium chloride, pH 7.4. The product was eluted from the column in reverse flow with 20 mM potassium phosphate, 200 mM sodium chloride pH 7.4. The column was stripped with 2 M sodium chloride, sanitized with 1 N sodium hydroxide and stored in 0.1 N sodium hydroxide at room temperature.

As part of the intermediate purification step 1, hydroxyapatite chromatography was performed. The hydroxyapatite chromatography step was operated as a flow-through chromatography step. The product obtained from the capture step above was loaded directly without any further adjustments onto a ceramic hydroxyapatite column (Bio-Rad Laboratories or equivalent) equilibrated with 400 mM potassium phosphate, 200 mM sodium chloride, pH 7.4, followed by 20 mM potassium phosphate, 200 mM sodium chloride, pH 7.4. Under the conditions of the chromatography, the product was collected in the flow-through fraction (HA product). The column was stripped with 400 mM potassium phosphate, 200 mM sodium chloride, pH 7.4, sanitized with 1 N sodium hydroxide and stored in 0.1 N sodium hydroxide at room temperature.

The percent pre-peak in the HA product from above was analyzed by high performance anion exchange chromatography. Table 8 and FIG. 7 show the percent pre-peak in HA product as a function of solubilization pH. As shown in Table 8 and FIG. 7, solubilizing the VH-PE38 and VL inclusion bodies at a lower pH leads to less deamidated CAT-8015 product. The capability of controlling CAT-8015 deamidation at an early step in the renaturation and purification process can increase overall process yield while maintaining the quality of the final purified drug substance.

TABLE 8

Percent Pre-Peak in HA Product as a Function of Solubilization pH

| Solubilization pH | 9.0 | 9.5 | 10.0 | 10.5 |
|---|---|---|---|---|
| Pre Peak (%) | 9.8 | 14.5 | 22.1 | 31.8 |

What is claimed is:

1. A method of producing a purified polypeptide from a solution comprising the polypeptide and a deamidated species of the polypeptide, wherein said deamidated species of the polypeptide results in an inhibition of potency of said polypeptide, the method comprising: (a) contacting the polypeptide with an anion exchange (AIEX) chromatography matrix; and (b) eluting the bound polypeptide from the AIEX chromatography matrix with a linear or step salt gradient, thereby separating said polypeptide from deamidated species of said polypeptide and producing a purified polypeptide having less than between about 25% and about 1% deamidated species;
   wherein the polypeptide comprises an antibody or antigen binding fragment thereof that binds the cell surface receptor CD22 and a *Pseudomonas* exotoxin, a cytotoxic fragment of *Pseudomonas* exotoxin, PE40, PE38, PE35, PE-LR, PE-LR-6X or PE-38.

2. The method of claim 1, wherein the AIEX matrix contains quaternary amine and tertiary amine ion exchange groups.

3. The method of claim 2, wherein the AIEX matrix contains a quaternary amino (Q) group.

4. The method of claim 3, wherein the AIEX matrix is Q sepharose.

5. The method of claim 1, wherein the polypeptide is eluted with a linear salt gradient that is from about 150 mM NaCl in Tris/HCl, pH 8.0 to about 300 mM NaCl in Tris/HCl, pH 8.0, from about 175 mM NaCl in Tris/HCl, pH 8.0 to about 275 mM NaCl in Tris/HCl, pH 8.0, or from about 192 mM NaCl in Tris/HCl, pH 8.0 to about 245 mM NaCl in Tris/HCl, pH 8.0.

6. The method of claim 1, wherein the antibody or antigen binding fragment comprises a Fab, a Fab', a F(ab')$_2$, a Fd, a single chain Fv or scFv, a disulfide linked Fv, a V-NAR domain, an IgNar, an intrabody, an IgGΔCH2, a minibody, a F(ab')$_3$, a tetrabody, a triabody, a diabody, a single-domain antibody, DVD-Ig, Fcab, mAb$^2$, a (scFv)$_2$, or a scFv-Fc.

7. The method of claim 1, wherein said *Pseudomonas* exotoxin has an amino acid sequence selected from the group consisting of SEQ ID NOs:16-22.

8. The method of claim 1, wherein said antibody or antigen binding fragment thereof comprises a VH and a VL sequence.

9. The method of claim 8, wherein said VH sequence is selected from the group consisting of SEQ ID NOs: 6-11.

10. The method of claim 8, wherein said VL sequence is selected from the group consisting of SEQ ID NOs: 2, and 12-15.

11. The method of claim 1, wherein the polypeptide is the CAT-8015 immunotoxin comprising the $V_H$-PE38 subunit of SEQ ID NO:1 and the $V_L$ subunit of SEQ ID NO:2.

12. A composition comprising a purified polypeptide having less than between about 25% and about 1% deamidated species, wherein said polypeptide is purified by the method of claim 1.

13. A pharmaceutical composition comprising the purified polypeptide of claim 12 and a pharmaceutically acceptable carrier.

14. A formulation comprising the composition of claim 12 and at least one excipient selected from the group consisting of sodium chloride, potassium dihydrogen phosphate, disodium hydrogen phosphate, and sodium hydroxide and water.

15. A method of modifying the bioactivity of a polypeptide solution comprising a polypeptide and a deamidated species of said polypeptide, the method comprising separating the polypeptide from the deamidated species by linear elution AIEX chromatography; and combining the purified polypeptide and deamidated species of said polypeptide in fixed quantities to obtain the desired bioactivity of the polypeptide solution.

16. The composition of claim 12, wherein the polypeptide is the CAT-8015 immunotoxin comprising the $V_H$-PE38 subunit of SEQ ID NO:1 and the $V_L$ subunit of SEQ ID NO:2.

* * * * *

UNITED STATES PATENT AND TRADEMARK OFFICE

(12)      CERTIFICATE EXTENDING PATENT TERM
UNDER 35 U.S.C. § 156

| | | | |
|---|---|---|---|
| (68) | PATENT NO. | : | 9,580,461 |
| (45) | ISSUED | : | February 28, 2017 |
| (75) | INVENTOR | : | Linke et al. |
| (73) | PATENT OWNER | : | MedImmune Limited |
| (95) | PRODUCT | : | LUMOXITI® (moxetumomab pasudotox-tdfk) |

This is to certify that an application under 35 U.S.C. § 156 has been filed in the United States Patent and Trademark Office, requesting extension of the term of U.S. Patent No. 9,580,461 based upon the regulatory review of the product LUMOXITI® (moxetumomab pasudotox-tdfk) by the Food and Drug Administration. According to United States Patent and Trademark Office records, the original expiration date of the patent as of the date of issuance of this certificate is April 4, 2032. Because it appears that the requirements of the law have been met, this certificate extends the term of the patent for the period of

(94)                                162 days subject to the payment of maintenance fees as provided by law, with all rights pertaining thereto as provided by 35 U.S.C. § 156.

I have caused the seal of the United States Patent and Trademark Office to be affixed this 7th day of January 2022.

Drew Hirshfeld
Commissioner for Patents, Performing the Functions and Duties of the Under Secretary of Commerce for Intellectual Property and Director of the United States Patent and Trademark Office

SEQUENCE LISTING

```
<160> NUMBER OF SEQ ID NOS: 23

<210> SEQ ID NO 1
<211> LENGTH: 476
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Glu Val Gln Leu Val Glu Ser Gly Gly Gly Leu Val Lys Pro Gly
1               5                   10                  15

Gly Ser Leu Lys Leu Ser Cys Ala Ala Ser Gly Phe Ala Phe Ser Ile
            20                  25                  30
```

```
Tyr Asp Met Ser Trp Val Arg Gln Thr Pro Glu Lys Cys Leu Glu Trp
         35                  40                  45

Val Ala Tyr Ile Ser Ser Gly Gly Thr Thr Tyr Tyr Pro Asp Thr
 50                  55                  60

Val Lys Gly Arg Phe Thr Ile Ser Arg Asp Asn Ala Lys Asn Thr Leu
 65                  70                  75                  80

Tyr Leu Gln Met Ser Ser Leu Lys Ser Glu Asp Thr Ala Met Tyr Tyr
                 85                  90                  95

Cys Ala Arg His Ser Gly Tyr Gly Thr His Trp Gly Val Leu Phe Ala
                100                 105                 110

Tyr Trp Gly Gln Gly Thr Leu Val Thr Val Ser Ala Lys Ala Ser Gly
                115                 120                 125

Gly Pro Glu Gly Gly Ser Leu Ala Ala Leu Thr Ala His Gln Ala Cys
        130                 135                 140

His Leu Pro Leu Glu Thr Phe Thr Arg His Arg Gln Pro Arg Gly Trp
145                 150                 155                 160

Glu Gln Leu Glu Gln Cys Gly Tyr Pro Val Gln Arg Leu Val Ala Leu
                165                 170                 175

Tyr Leu Ala Ala Arg Leu Ser Trp Asn Gln Val Asp Gln Val Ile Arg
                180                 185                 190

Asn Ala Leu Ala Ser Pro Gly Ser Gly Gly Asp Leu Gly Glu Ala Ile
                195                 200                 205

Arg Glu Gln Pro Glu Gln Ala Arg Leu Ala Leu Thr Leu Ala Ala Ala
        210                 215                 220

Glu Ser Glu Arg Phe Val Arg Gln Gly Thr Gly Asn Asp Glu Ala Gly
225                 230                 235                 240

Ala Ala Asn Gly Pro Ala Asp Ser Gly Asp Ala Leu Leu Glu Arg Asn
                245                 250                 255

Tyr Pro Thr Gly Ala Glu Phe Leu Gly Asp Gly Gly Asp Val Ser Phe
                260                 265                 270

Ser Thr Arg Gly Thr Gln Asn Trp Thr Val Glu Arg Leu Leu Gln Ala
        275                 280                 285

His Arg Gln Leu Glu Glu Arg Gly Tyr Val Phe Val Gly Tyr His Gly
        290                 295                 300

Thr Phe Leu Glu Ala Ala Gln Ser Ile Val Phe Gly Gly Val Arg Ala
305                 310                 315                 320

Arg Ser Gln Asp Leu Asp Ala Ile Trp Arg Gly Phe Tyr Ile Ala Gly
                325                 330                 335

Asp Pro Ala Leu Ala Tyr Gly Tyr Ala Gln Asp Gln Glu Pro Asp Ala
                340                 345                 350

Arg Gly Arg Ile Arg Asn Gly Ala Leu Leu Arg Val Tyr Val Pro Arg
        355                 360                 365

Ser Ser Leu Pro Gly Phe Tyr Arg Thr Ser Leu Thr Leu Ala Ala Pro
        370                 375                 380

Glu Ala Ala Gly Glu Val Glu Arg Leu Ile Gly His Pro Leu Pro Leu
385                 390                 395                 400

Arg Leu Asp Ala Ile Thr Gly Pro Glu Glu Gly Gly Arg Leu Glu
                405                 410                 415

Thr Ile Leu Gly Trp Pro Leu Ala Glu Arg Thr Val Val Ile Pro Ser
                420                 425                 430

Ala Ile Pro Thr Asp Pro Arg Asn Val Gly Gly Asp Leu Asp Pro Ser
                435                 440                 445
```

```
Ser Ile Pro Asp Lys Glu Gln Ala Ile Ser Ala Leu Pro Asp Tyr Ala
        450                 455                 460
Ser Gln Pro Gly Lys Pro Pro Arg Glu Asp Leu Lys
465                 470                 475

<210> SEQ ID NO 2
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Asp Ile Gln Met Thr Gln Thr Thr Ser Ser Leu Ser Ala Ser Leu
1               5                   10                  15

Gly Asp Arg Val Thr Ile Ser Cys Arg Ala Ser Gln Asp Ile Ser Asn
            20                  25                  30

Tyr Leu Asn Trp Tyr Gln Gln Lys Pro Asp Gly Thr Val Lys Leu Leu
        35                  40                  45

Ile Tyr Tyr Thr Ser Ile Leu His Ser Gly Val Pro Ser Arg Phe Ser
    50                  55                  60

Gly Ser Gly Ser Gly Thr Asp Tyr Ser Leu Thr Ile Ser Asn Leu Glu
65                  70                  75                  80

Gln Glu Asp Phe Ala Thr Tyr Phe Cys Gln Gln Gly Asn Thr Leu Pro
                85                  90                  95

Trp Thr Phe Gly Cys Gly Thr Lys Leu Glu Ile Lys
            100                 105

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Lys Asp Glu Leu
1

<210> SEQ ID NO 4
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Arg Glu Asp Leu
1

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Arg Glu Asp Leu Lys
1               5
```

<210> SEQ ID NO 6
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Met Glu Val Gln Leu Val Glu Ser Gly Gly Gly Leu Val Lys Pro Gly
1               5                   10                  15

Gly Ser Leu Lys Leu Ser Cys Ala Ala Ser Gly Phe Ala Phe Ser Ile
            20                  25                  30

Tyr Asp Met Ser Trp Val Arg Gln Thr Pro Glu Lys Cys Leu Glu Trp
        35                  40                  45

Val Ala Tyr Ile Ser Ser Gly Gly Thr Thr Tyr Tyr Pro Asp Thr
    50                  55                  60

Val Lys Gly Arg Phe Thr Ile Ser Arg Asp Asn Ala Lys Asn Thr Leu
65                  70                  75                  80

Tyr Leu Gln Met Ser Ser Leu Lys Ser Glu Asp Thr Ala Met Tyr Tyr
                85                  90                  95

Cys Ala Arg His Ser Gly Tyr Gly Thr His Trp Gly Val Leu Phe Ala
            100                 105                 110

Tyr Trp Gly Gln Gly Thr Leu Val Thr Val Ser Ala
            115                 120

<210> SEQ ID NO 7
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Met Glu Val Gln Leu Val Glu Ser Gly Gly Gly Leu Val Lys Pro Gly
1               5                   10                  15

Gly Ser Leu Lys Leu Ser Cys Ala Ala Ser Gly Phe Ala Phe Ser Ile
            20                  25                  30

Tyr Asp Met Ser Trp Val Arg Gln Thr Pro Glu Lys Cys Leu Glu Trp
        35                  40                  45

Val Ala Tyr Ile Ser Ser Gly Gly Thr Thr Tyr Tyr Pro Asp Thr
    50                  55                  60

Val Lys Gly Arg Phe Thr Ile Ser Arg Asp Asn Ala Lys Asn Thr Leu
65                  70                  75                  80

Tyr Leu Gln Met Ser Ser Leu Lys Ser Glu Asp Thr Ala Met Tyr Tyr
                85                  90                  95

Cys Ala Arg His Ser Gly Tyr Gly Tyr Asn Trp Gly Val Leu Phe Ala
            100                 105                 110

Tyr Trp Gly Gln Gly Thr Leu Val Thr Val Ser Ala
            115                 120

<210> SEQ ID NO 8
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Met Glu Val Gln Leu Val Glu Ser Gly Gly Gly Leu Val Lys Pro Gly
1               5                   10                  15

Gly Ser Leu Lys Leu Ser Cys Ala Ala Ser Gly Phe Ala Phe Ser Ile
            20                  25                  30

Tyr Asp Met Ser Trp Val Arg Gln Thr Pro Glu Lys Cys Leu Glu Trp
        35                  40                  45

Val Ala Tyr Ile Ser Ser Gly Gly Thr Thr Tyr Tyr Pro Asp Thr
    50                  55                  60

Val Lys Gly Arg Phe Thr Ile Ser Arg Asp Asn Ala Lys Asn Thr Leu
65                  70                  75                  80

Tyr Leu Gln Met Ser Ser Leu Lys Ser Glu Asp Thr Ala Met Tyr Tyr
                85                  90                  95

Cys Ala Arg His Ser Gly Tyr Gly Thr Thr Trp Gly Val Leu Phe Ala
            100                 105                 110

Tyr Trp Gly Gln Gly Thr Leu Val Thr Val Ser Ala
        115                 120

<210> SEQ ID NO 9
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Met Glu Val Gln Leu Val Glu Ser Gly Gly Gly Leu Val Lys Pro Gly
1               5                   10                  15

Gly Ser Leu Lys Leu Ser Cys Ala Ala Ser Gly Phe Ala Phe Ser Ile
            20                  25                  30

Tyr Asp Met Ser Trp Val Arg Gln Thr Pro Glu Lys Cys Leu Glu Trp
        35                  40                  45

Val Ala Tyr Ile Ser Ser Gly Gly Thr Thr Tyr Tyr Pro Asp Thr
    50                  55                  60

Val Lys Gly Arg Phe Thr Ile Ser Arg Asp Asn Ala Lys Asn Thr Leu
65                  70                  75                  80

Tyr Leu Gln Met Ser Ser Leu Lys Ser Glu Asp Thr Ala Met Tyr Tyr
                85                  90                  95

Cys Ala Arg His Ser Gly Tyr Gly Ser Thr Tyr Gly Val Leu Phe Ala
            100                 105                 110

Tyr Trp Gly Gln Gly Thr Leu Val Thr Val Ser Ala
        115                 120

<210> SEQ ID NO 10
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Met Glu Val Gln Leu Val Glu Ser Gly Gly Gly Leu Val Lys Pro Gly
1               5                   10                  15

Gly Ser Leu Lys Leu Ser Cys Ala Ala Ser Gly Phe Ala Phe Ser Ile
            20                  25                  30

Tyr Asp Met Ser Trp Val Arg Gln Thr Pro Glu Lys Cys Leu Glu Trp
            35                  40                  45

Val Ala Tyr Ile Ser Ser Gly Gly Thr Thr Tyr Tyr Pro Asp Thr
 50                  55                  60

Val Lys Gly Arg Phe Thr Ile Ser Arg Asp Asn Ala Lys Asn Thr Leu
 65                  70                  75                  80

Tyr Leu Gln Met Ser Ser Leu Lys Ser Glu Asp Thr Ala Met Tyr Tyr
                85                  90                  95

Cys Ala Arg His Ser Gly Tyr Gly Thr His Trp Gly Val Leu Phe Ala
                100                 105                 110

Tyr Trp Gly Gln Gly Thr Leu Val Thr Val Ser Ala
            115                 120

<210> SEQ ID NO 11
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Met Glu Val Gln Leu Val Glu Ser Gly Gly Gly Leu Val Lys Pro Gly
 1               5                   10                  15

Gly Ser Leu Lys Leu Ser Cys Ala Ala Ser Gly Phe Ala Phe Ser Ile
            20                  25                  30

Tyr Asp Met Ser Trp Val Arg Gln Thr Pro Glu Lys Cys Leu Glu Trp
            35                  40                  45

Val Ala Tyr Ile Ser Ser Gly Gly Thr Thr Tyr Tyr Pro Asp Thr
 50                  55                  60

Val Lys Gly Arg Phe Thr Ile Ser Arg Asp Asn Ala Lys Asn Thr Leu
 65                  70                  75                  80

Tyr Leu Gln Met Ser Ser Leu Lys Ser Glu Asp Thr Ala Met Tyr Tyr
                85                  90                  95

Cys Ala Arg His Ser Gly Tyr Gly Ser Ser Tyr Gly Val Leu Phe Ala
                100                 105                 110

Tyr Trp Gly Gln Gly Thr Leu Val Thr Val Ser Ala
            115                 120

<210> SEQ ID NO 12
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Met Asp Ile Gln Met Thr Gln Thr Thr Ser Ser Leu Ser Ala Ser Leu
 1               5                   10                  15

Gly Asp Arg Val Thr Ile Ser Cys Arg Ala Ser Gln Asp Ile Ala Arg
            20                  25                  30

Tyr Leu Asn Trp Tyr Gln Gln Lys Pro Asp Gly Thr Val Lys Leu Leu
            35                  40                  45

Ile Tyr Tyr Thr Ser Ile Leu His Ser Gly Val Pro Ser Arg Phe Ser
 50                  55                  60

Gly Ser Gly Ser Gly Thr Asp Tyr Ser Leu Thr Ile Ser Asn Leu Glu
 65                  70                  75                  80

Gln Glu Asp Phe Ala Thr Tyr Phe Cys Gln Gln Gly Asn Thr Leu Pro
                85                  90                  95

Trp Thr Phe Gly Cys Gly Thr Lys Leu Glu Ile Lys
            100                 105

<210> SEQ ID NO 13
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Met Asp Ile Gln Met Thr Gln Thr Thr Ser Ser Leu Ser Ala Ser Leu
1               5                   10                  15

Gly Asp Arg Val Thr Ile Ser Cys Arg Ala Ser Gln Asp Ile His Gly
            20                  25                  30

Tyr Leu Asn Trp Tyr Gln Gln Lys Pro Asp Gly Thr Val Lys Leu Leu
        35                  40                  45

Ile Tyr Tyr Thr Ser Ile Leu His Ser Gly Val Pro Ser Arg Phe Ser
    50                  55                  60

Gly Ser Gly Ser Gly Thr Asp Tyr Ser Leu Thr Ile Ser Asn Leu Glu
65                  70                  75                  80

Gln Glu Asp Phe Ala Thr Tyr Phe Cys Gln Gln Gly Asn Thr Leu Pro
                85                  90                  95

Trp Thr Phe Gly Cys Gly Thr Lys Leu Glu Ile Lys
            100                 105

<210> SEQ ID NO 14
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Met Asp Ile Gln Met Thr Gln Thr Thr Ser Ser Leu Ser Ala Ser Leu
1               5                   10                  15

Gly Asp Arg Val Thr Ile Ser Cys Arg Ala Ser Gln Asp Ile Gly Arg
            20                  25                  30

Tyr Leu Asn Trp Tyr Gln Gln Lys Pro Asp Gly Thr Val Lys Leu Leu
        35                  40                  45

Ile Tyr Tyr Thr Ser Ile Leu His Ser Gly Val Pro Ser Arg Phe Ser
    50                  55                  60

Gly Ser Gly Ser Gly Thr Asp Tyr Ser Leu Thr Ile Ser Asn Leu Glu
65                  70                  75                  80

Gln Glu Asp Phe Ala Thr Tyr Phe Cys Gln Gln Gly Asn Thr Leu Pro
                85                  90                  95

Trp Thr Phe Gly Cys Gly Thr Lys Leu Glu Ile Lys
            100                 105

<210> SEQ ID NO 15
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 15

Met Asp Ile Gln Met Thr Gln Thr Thr Ser Ser Leu Ser Ala Ser Leu
1               5                   10                  15

Gly Asp Arg Val Thr Ile Ser Cys Arg Ala Ser Gln Asp Ile Arg Gly
            20                  25                  30

Tyr Leu Asn Trp Tyr Gln Gln Lys Pro Asp Gly Thr Val Lys Leu Leu
        35                  40                  45

Ile Tyr Tyr Thr Ser Ile Leu His Ser Gly Val Pro Ser Arg Phe Ser
    50                  55                  60

Gly Ser Gly Ser Gly Thr Asp Tyr Ser Leu Thr Ile Ser Asn Leu Glu
65                  70                  75                  80

Gln Glu Asp Phe Ala Thr Tyr Phe Cys Gln Gln Gly Asn Thr Leu Pro
                85                  90                  95

Trp Thr Phe Gly Cys Gly Thr Lys Leu Glu Ile Lys
            100                 105

<210> SEQ ID NO 16
<211> LENGTH: 597
<212> TYPE: PRT
<213> ORGANISM: Pseudomonas aeruginosa

<400> SEQUENCE: 16

Ala Glu Glu Ala Phe Asp Leu Trp Asn Glu Cys Ala Lys Ala Cys Val
1               5                   10                  15

Leu Asp Leu Lys Asp Gly Val Arg Ser Ser Arg Met Ser Val Asp Pro
            20                  25                  30

Ala Ile Ala Asp Thr Asn Gly Gln Gly Val Leu His Tyr Ser Met Val
        35                  40                  45

Leu Glu Gly Gly Asn Asp Ala Leu Lys Leu Ala Ile Asp Asn Ala Leu
    50                  55                  60

Ser Ile Thr Ser Asp Gly Leu Thr Ile Arg Leu Glu Gly Gly Val Glu
65                  70                  75                  80

Pro Asn Lys Pro Val Arg Tyr Ser Tyr Thr Arg Gln Ala Arg Gly Ser
                85                  90                  95

Trp Ser Leu Asn Trp Leu Val Pro Ile Gly His Glu Lys Pro Ser Asn
            100                 105                 110

Ile Lys Val Phe Ile His Glu Leu Asn Ala Gly Asn Gln Leu Ser His
        115                 120                 125

Met Ser Pro Ile Tyr Thr Ile Glu Met Gly Asp Glu Leu Leu Ala Lys
    130                 135                 140

Leu Ala Arg Asp Ala Thr Phe Phe Val Arg Ala His Glu Ser Asn Glu
145                 150                 155                 160

Met Gln Pro Thr Leu Ala Ile Ser His Ala Gly Val Ser Val Val Met
                165                 170                 175

Ala Gln Thr Gln Pro Arg Arg Glu Lys Arg Trp Ser Glu Trp Ala Ser
            180                 185                 190

Gly Lys Val Leu Cys Leu Leu Asp Pro Leu Asp Gly Val Tyr Asn Tyr
        195                 200                 205

Leu Ala Gln Gln Arg Cys Asn Leu Asp Asp Thr Trp Glu Gly Lys Ile
    210                 215                 220

Tyr Arg Val Leu Ala Gly Asn Pro Ala Lys His Asp Leu Asp Ile Lys
225                 230                 235                 240

Pro Thr Val Ile Ser His Arg Leu His Phe Pro Glu Gly Gly Ser Leu
                245                 250                 255
```

Ala Ala Leu Thr Ala His Gln Ala Cys His Leu Pro Leu Glu Thr Phe
            260                 265                 270

Thr Arg His Arg Gln Pro Arg Gly Trp Glu Gln Leu Glu Gln Cys Gly
        275                 280                 285

Tyr Pro Val Gln Arg Leu Val Ala Leu Tyr Leu Ala Ala Arg Leu Ser
    290                 295                 300

Trp Asn Gln Val Asp Gln Val Ile Arg Asn Ala Leu Ala Ser Pro Gly
305                 310                 315                 320

Ser Gly Gly Asp Leu Gly Glu Ala Ile Arg Glu Gln Pro Glu Gln Ala
                325                 330                 335

Arg Leu Ala Leu Thr Leu Ala Ala Glu Ser Glu Arg Phe Val Arg
            340                 345                 350

Gln Gly Thr Gly Asn Asp Glu Ala Gly Ala Ala Asn Gly Pro Ala Asp
        355                 360                 365

Ser Gly Asp Ala Leu Leu Glu Arg Asn Tyr Pro Thr Gly Ala Glu Phe
    370                 375                 380

Leu Gly Asp Gly Gly Asp Val Ser Phe Ser Thr Arg Gly Thr Gln Asn
385                 390                 395                 400

Trp Thr Val Glu Arg Leu Leu Gln Ala His Arg Gln Leu Glu Glu Arg
                405                 410                 415

Gly Tyr Val Phe Val Gly Tyr His Gly Thr Phe Leu Glu Ala Ala Gln
            420                 425                 430

Ser Ile Val Phe Gly Gly Val Arg Ala Arg Ser Gln Asp Leu Asp Ala
        435                 440                 445

Ile Trp Arg Gly Phe Tyr Ile Ala Gly Asp Pro Ala Leu Ala Tyr Gly
    450                 455                 460

Tyr Ala Gln Asp Gln Glu Pro Asp Ala Arg Gly Arg Ile Arg Asn Gly
465                 470                 475                 480

Ala Leu Leu Arg Val Tyr Val Pro Arg Ser Ser Leu Pro Gly Phe Tyr
                485                 490                 495

Arg Thr Ser Leu Thr Leu Ala Ala Pro Glu Ala Ala Gly Glu Val Glu
            500                 505                 510

Arg Leu Ile Gly His Pro Leu Pro Leu Arg Leu Asp Ala Ile Thr Gly
        515                 520                 525

Pro Glu Glu Glu Gly Gly Arg Leu Glu Thr Ile Leu Gly Trp Pro Leu
    530                 535                 540

Ala Glu Arg Thr Val Val Ile Pro Ser Ala Ile Pro Thr Asp Pro Arg
545                 550                 555                 560

Asn Val Gly Gly Asp Leu Asp Pro Ser Ser Ile Pro Asp Lys Glu Gln
                565                 570                 575

Ala Ile Ser Ala Leu Pro Asp Tyr Ala Ser Gln Pro Gly Lys Pro Pro
            580                 585                 590

Arg Glu Asp Leu Lys
        595

<210> SEQ ID NO 17
<211> LENGTH: 361
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Gly Gly Ser Leu Ala Ala Leu Thr Ala His Gln Ala Cys His Leu Pro
1               5                   10                  15

Leu Glu Thr Phe Thr Arg His Arg Gln Pro Arg Gly Trp Glu Gln Leu
             20                  25                  30

Glu Gln Cys Gly Tyr Pro Val Gln Arg Leu Val Ala Leu Tyr Leu Ala
         35                  40                  45

Ala Arg Leu Ser Trp Asn Gln Val Asp Gln Val Ile Arg Asn Ala Leu
 50                  55                  60

Ala Ser Pro Gly Ser Gly Gly Asp Leu Gly Glu Ala Ile Arg Glu Gln
 65                  70                  75                  80

Pro Glu Gln Ala Arg Leu Ala Leu Thr Leu Ala Ala Ala Glu Ser Glu
                 85                  90                  95

Arg Phe Val Arg Gln Gly Thr Gly Asn Asp Glu Ala Gly Ala Ala Asn
             100                 105                 110

Ala Asp Val Val Ser Leu Thr Cys Pro Val Ala Ala Gly Glu Cys Ala
             115                 120                 125

Gly Pro Ala Asp Ser Gly Asp Ala Leu Leu Glu Arg Asn Tyr Pro Thr
130                 135                 140

Gly Ala Glu Phe Leu Gly Asp Gly Gly Asp Val Ser Phe Ser Thr Arg
145                 150                 155                 160

Gly Thr Gln Asn Trp Thr Val Glu Arg Leu Leu Gln Ala His Arg Gln
                 165                 170                 175

Leu Glu Glu Arg Gly Tyr Val Phe Val Gly Tyr His Gly Thr Phe Leu
             180                 185                 190

Glu Ala Ala Gln Ser Ile Val Phe Gly Gly Val Arg Ala Arg Ser Gln
         195                 200                 205

Asp Leu Asp Ala Ile Trp Arg Gly Phe Tyr Ile Ala Gly Asp Pro Ala
210                 215                 220

Leu Ala Tyr Gly Tyr Ala Gln Asp Gln Glu Pro Asp Ala Arg Gly Arg
225                 230                 235                 240

Ile Arg Asn Gly Ala Leu Leu Arg Val Tyr Val Pro Arg Ser Ser Leu
                 245                 250                 255

Pro Gly Phe Tyr Arg Thr Ser Leu Thr Leu Ala Ala Pro Glu Ala Ala
             260                 265                 270

Gly Glu Val Glu Arg Leu Ile Gly His Pro Leu Pro Leu Arg Leu Asp
         275                 280                 285

Ala Ile Thr Gly Pro Glu Glu Glu Gly Gly Arg Leu Glu Thr Ile Leu
290                 295                 300

Gly Trp Pro Leu Ala Glu Arg Thr Val Val Ile Pro Ser Ala Ile Pro
305                 310                 315                 320

Thr Asp Pro Arg Asn Val Gly Gly Asp Leu Asp Pro Ser Ser Ile Pro
                 325                 330                 335

Asp Lys Glu Gln Ala Ile Ser Ala Leu Pro Asp Tyr Ala Ser Gln Pro
             340                 345                 350

Gly Lys Pro Pro Arg Glu Asp Leu Lys
         355                 360

<210> SEQ ID NO 18
<211> LENGTH: 345
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Gly Gly Ser Leu Ala Ala Leu Thr Ala His Gln Ala Cys His Leu Pro

```
                1               5                  10                  15
        Leu Glu Thr Phe Thr Arg His Arg Gln Pro Arg Gly Trp Glu Gln Leu
                        20                  25                  30

Glu Gln Cys Gly Tyr Pro Val Gln Arg Leu Val Ala Leu Tyr Leu Ala
                    35                  40                  45

Ala Arg Leu Ser Trp Asn Gln Val Asp Gln Val Ile Arg Asn Ala Leu
                50                  55                  60

Ala Ser Pro Gly Ser Gly Gly Asp Leu Gly Glu Ala Ile Arg Glu Gln
        65                  70                  75                  80

Pro Glu Gln Ala Arg Leu Ala Leu Thr Leu Ala Ala Ala Glu Ser Glu
                        85                  90                  95

Arg Phe Val Arg Gln Gly Thr Gly Asn Asp Glu Ala Gly Ala Ala Asn
                    100                 105                 110

Gly Pro Ala Asp Ser Gly Asp Ala Leu Leu Glu Arg Asn Tyr Pro Thr
                115                 120                 125

Gly Ala Glu Phe Leu Gly Asp Gly Gly Asp Val Ser Phe Ser Thr Arg
        130                 135                 140

Gly Thr Gln Asn Trp Thr Val Glu Arg Leu Leu Gln Ala His Arg Gln
        145                 150                 155                 160

Leu Glu Glu Arg Gly Tyr Val Phe Val Gly Tyr His Gly Thr Phe Leu
                        165                 170                 175

Glu Ala Ala Gln Ser Ile Val Phe Gly Gly Val Arg Ala Arg Ser Gln
                    180                 185                 190

Asp Leu Asp Ala Ile Trp Arg Gly Phe Tyr Ile Ala Gly Asp Pro Ala
                195                 200                 205

Leu Ala Tyr Gly Tyr Ala Gln Asp Gln Glu Pro Asp Ala Arg Gly Arg
        210                 215                 220

Ile Arg Asn Gly Ala Leu Leu Arg Val Tyr Val Pro Arg Ser Ser Leu
        225                 230                 235                 240

Pro Gly Phe Tyr Arg Thr Ser Leu Thr Leu Ala Ala Pro Glu Ala Ala
                        245                 250                 255

Gly Glu Val Glu Arg Leu Ile Gly His Pro Leu Pro Leu Arg Leu Asp
                    260                 265                 270

Ala Ile Thr Gly Pro Glu Glu Gly Gly Arg Leu Glu Thr Ile Leu
                275                 280                 285

Gly Trp Pro Leu Ala Glu Arg Thr Val Val Ile Pro Ser Ala Ile Pro
        290                 295                 300

Thr Asp Pro Arg Asn Val Gly Gly Asp Leu Asp Pro Ser Ser Ile Pro
        305                 310                 315                 320

Asp Lys Glu Gln Ala Ile Ser Ala Leu Pro Asp Tyr Ala Ser Gln Pro
                        325                 330                 335

Gly Lys Pro Pro Arg Glu Asp Leu Lys
                    340                 345

<210> SEQ ID NO 19
<211> LENGTH: 318
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Met Trp Glu Gln Leu Glu Gln Cys Gly Tyr Pro Val Gln Arg Leu Val
1               5                   10                  15
```

```
Ala Leu Tyr Leu Ala Ala Arg Leu Ser Trp Asn Gln Val Asp Gln Val
            20                  25                  30

Ile Arg Asn Ala Leu Ala Ser Pro Gly Ser Gly Gly Asp Leu Gly Glu
        35                  40                  45

Ala Ile Arg Glu Gln Pro Glu Gln Ala Arg Leu Ala Leu Thr Leu Ala
    50                  55                  60

Ala Ala Glu Ser Glu Arg Phe Val Arg Gln Gly Thr Gly Asn Asp Glu
65                  70                  75                  80

Ala Gly Ala Ala Asn Gly Pro Ala Asp Ser Gly Asp Ala Leu Leu Glu
                85                  90                  95

Arg Asn Tyr Pro Thr Gly Ala Glu Phe Leu Gly Asp Gly Gly Asp Val
            100                 105                 110

Ser Phe Ser Thr Arg Gly Thr Gln Asn Trp Thr Val Glu Arg Leu Leu
        115                 120                 125

Gln Ala His Arg Gln Leu Glu Glu Arg Gly Tyr Val Phe Val Gly Tyr
    130                 135                 140

His Gly Thr Phe Leu Glu Ala Ala Gln Ser Ile Val Phe Gly Gly Val
145                 150                 155                 160

Arg Ala Arg Ser Gln Asp Leu Asp Ala Ile Trp Arg Gly Phe Tyr Ile
                165                 170                 175

Ala Gly Asp Pro Ala Leu Ala Tyr Gly Tyr Ala Gln Asp Gln Glu Pro
            180                 185                 190

Asp Ala Arg Gly Arg Ile Arg Asn Gly Ala Leu Leu Arg Val Tyr Val
        195                 200                 205

Pro Arg Ser Ser Leu Pro Gly Phe Tyr Arg Thr Ser Leu Thr Leu Ala
    210                 215                 220

Ala Pro Glu Ala Ala Gly Glu Val Glu Arg Leu Ile Gly His Pro Leu
225                 230                 235                 240

Pro Leu Arg Leu Asp Ala Ile Thr Gly Pro Glu Glu Gly Gly Arg
                245                 250                 255

Leu Glu Thr Ile Leu Gly Trp Pro Leu Ala Glu Arg Thr Val Val Ile
            260                 265                 270

Pro Ser Ala Ile Pro Thr Asp Pro Arg Asn Val Gly Gly Asp Leu Asp
        275                 280                 285

Pro Ser Ser Ile Pro Asp Lys Glu Gln Ala Ile Ser Ala Leu Pro Asp
    290                 295                 300

Tyr Ala Ser Gln Pro Gly Lys Pro Pro Arg Glu Asp Leu Lys
305                 310                 315

<210> SEQ ID NO 20
<211> LENGTH: 230
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Arg His Arg Gln Pro Arg Gly Trp Glu Gln Leu Pro Thr Gly Ala Glu
1               5                   10                  15

Phe Leu Gly Asp Gly Gly Asp Val Ser Phe Ser Thr Arg Gly Thr Gln
            20                  25                  30

Asn Trp Thr Val Glu Arg Leu Leu Gln Ala His Arg Gln Leu Glu Glu
        35                  40                  45

Arg Gly Tyr Val Phe Val Gly Tyr His Gly Thr Phe Leu Glu Ala Ala
    50                  55                  60
```

Gln Ser Ile Val Phe Gly Val Arg Ala Arg Ser Gln Asp Leu Asp
65                  70                  75                  80

Ala Ile Trp Arg Gly Phe Tyr Ile Ala Gly Asp Pro Ala Leu Ala Tyr
                85                  90                  95

Gly Tyr Ala Gln Asp Gln Glu Pro Asp Ala Arg Gly Arg Ile Arg Asn
            100                 105                 110

Gly Ala Leu Leu Arg Val Tyr Val Pro Arg Ser Ser Leu Pro Gly Phe
            115                 120                 125

Tyr Arg Thr Ser Leu Thr Leu Ala Ala Pro Glu Ala Ala Gly Glu Val
130                 135                 140

Glu Arg Leu Ile Gly His Pro Leu Pro Leu Arg Leu Asp Ala Ile Thr
145                 150                 155                 160

Gly Pro Glu Glu Gly Gly Arg Leu Glu Thr Ile Leu Gly Trp Pro
                165                 170                 175

Leu Ala Glu Arg Thr Val Val Ile Pro Ser Ala Ile Pro Thr Asp Pro
                180                 185                 190

Arg Asn Val Gly Gly Asp Leu Asp Pro Ser Ser Ile Pro Asp Lys Glu
            195                 200                 205

Gln Ala Ile Ser Ala Leu Pro Asp Tyr Ala Ser Gln Pro Gly Lys Pro
    210                 215                 220

Pro Arg Glu Asp Leu Lys
225                 230

<210> SEQ ID NO 21
<211> LENGTH: 230
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Arg His Arg Gln Pro Arg Gly Trp Glu Gln Leu Pro Thr Gly Ala Glu
1               5                   10                  15

Phe Leu Gly Asp Gly Gly Asp Val Ser Phe Ser Thr Arg Gly Thr Gln
                20                  25                  30

Asn Trp Thr Val Glu Arg Leu Leu Gln Ala His Arg Gln Leu Glu Glu
            35                  40                  45

Gly Gly Tyr Val Phe Val Gly Tyr His Gly Thr Phe Leu Glu Ala Ala
        50                  55                  60

Gln Ser Ile Val Phe Gly Val Arg Ala Arg Ser Gln Asp Leu Asp
65                  70                  75                  80

Ala Ile Trp Ala Gly Phe Tyr Ile Ala Gly Asp Pro Ala Leu Ala Tyr
                85                  90                  95

Gly Tyr Ala Gln Asp Gln Glu Pro Asp Ala Ala Gly Arg Ile Arg Asn
            100                 105                 110

Gly Ala Leu Leu Arg Val Tyr Val Pro Arg Ser Ser Leu Pro Gly Phe
            115                 120                 125

Tyr Ala Thr Ser Leu Thr Leu Ala Ala Pro Glu Ala Ala Gly Glu Val
130                 135                 140

Glu Arg Leu Ile Gly His Pro Leu Pro Leu Arg Leu Asp Ala Ile Thr
145                 150                 155                 160

Gly Pro Glu Glu Ala Gly Gly Arg Leu Glu Thr Ile Leu Gly Trp Pro
                165                 170                 175

Leu Ala Glu Arg Thr Val Val Ile Pro Ser Ala Ile Pro Thr Asp Pro

```
                    180                 185                 190

Arg Asn Val Gly Gly Asp Leu Asp Pro Ser Ser Ile Pro Asp Ser Glu
            195                 200                 205

Gln Ala Ile Ser Ala Leu Pro Asp Tyr Ala Ser Gln Pro Gly Lys Pro
        210                 215                 220

Pro Arg Glu Asp Leu Lys
225                 230

<210> SEQ ID NO 22
<211> LENGTH: 347
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Pro Glu Gly Gly Ser Leu Ala Ala Leu Thr Ala His Gln Ala Cys His
1               5                   10                  15

Leu Pro Leu Glu Thr Phe Thr Arg His Arg Gln Pro Arg Gly Trp Glu
            20                  25                  30

Gln Leu Glu Gln Cys Gly Tyr Pro Val Gln Arg Leu Val Ala Leu Tyr
        35                  40                  45

Leu Ala Ala Arg Leu Ser Trp Asn Gln Val Asp Gln Val Ile Arg Asn
    50                  55                  60

Ala Leu Ala Ser Pro Gly Ser Gly Gly Asp Leu Gly Glu Ala Ile Arg
65                  70                  75                  80

Glu Gln Pro Glu Gln Ala Arg Leu Ala Leu Thr Leu Ala Ala Ala Glu
                85                  90                  95

Ser Glu Arg Phe Val Arg Gln Gly Thr Gly Asn Asp Glu Ala Gly Ala
            100                 105                 110

Ala Asn Gly Pro Ala Asp Ser Gly Asp Ala Leu Leu Glu Arg Asn Tyr
        115                 120                 125

Pro Thr Gly Ala Glu Phe Leu Gly Asp Gly Gly Asp Val Ser Phe Ser
    130                 135                 140

Thr Arg Gly Thr Gln Asn Trp Thr Val Glu Arg Leu Leu Gln Ala His
145                 150                 155                 160

Arg Gln Leu Glu Glu Arg Gly Tyr Val Phe Val Gly Tyr His Gly Thr
                165                 170                 175

Phe Leu Glu Ala Ala Gln Ser Ile Val Phe Gly Gly Val Arg Ala Arg
            180                 185                 190

Ser Gln Asp Leu Asp Ala Ile Trp Arg Gly Phe Tyr Ile Ala Gly Asp
        195                 200                 205

Pro Ala Leu Ala Tyr Gly Tyr Ala Gln Asp Gln Glu Pro Asp Ala Arg
    210                 215                 220

Gly Arg Ile Arg Asn Gly Ala Leu Leu Arg Val Tyr Val Pro Arg Ser
225                 230                 235                 240

Ser Leu Pro Gly Phe Tyr Arg Thr Ser Leu Thr Leu Ala Ala Pro Glu
                245                 250                 255

Ala Ala Gly Glu Val Glu Arg Leu Ile Gly His Pro Leu Pro Leu Arg
            260                 265                 270

Leu Asp Ala Ile Thr Gly Pro Glu Glu Gly Gly Arg Leu Glu Thr
        275                 280                 285

Ile Leu Gly Trp Pro Leu Ala Glu Arg Thr Val Val Ile Pro Ser Ala
    290                 295                 300
```

```
Ile Pro Thr Asp Pro Arg Asn Val Gly Gly Asp Leu Asp Pro Ser Ser
305                 310                 315                 320

Ile Pro Asp Lys Glu Gln Ala Ile Ser Ala Leu Pro Asp Tyr Ala Ser
                325                 330                 335

Gln Pro Gly Lys Pro Pro Arg Glu Asp Leu Lys
            340                 345

<210> SEQ ID NO 23
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Lys Ala Ser Gly Gly
1               5
```